(12) United States Patent
Gambale

(10) Patent No.: US 6,231,564 B1
(45) Date of Patent: *May 15, 2001

(54) STORABLE GUIDEWIRE SYSTEM

(75) Inventor: Richard A. Gambale, Tyngsboro, MA (US)

(73) Assignee: Medtronic AVE, Inc., Santa Rosa, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/536,954

(22) Filed: Sep. 29, 1995

(51) Int. Cl.[7] .................. A61M 25/01; A61M 25/02; A61M 25/04; A61M 25/06; A61M 25/08; A61M 25/09; A61M 25/082; A61M 25/085; A61M 25/088; A61M 25/095; A61M 25/098

(52) U.S. Cl. .................................. 604/528; 600/585

(58) Field of Search ..................... 604/95, 170, 174, 604/177, 178, 156, 164, 165, 159, 160, 208, 281, 158, 283, 264, 282; 606/1, 108; 128/772, 656, 657, 658; 206/305, 363, 364, 370, 349, 389, 388, 825, 438, 409, 407, 569–572; 242/388, 389, 398, 396, 223, 397

(56) References Cited

U.S. PATENT DOCUMENTS

| 3,683,928 | 8/1972 | Kuntz . |
| 3,774,605 | 11/1973 | Jewett . |
| 3,826,256 | 7/1974 | Smith . |
| 3,835,854 | 9/1974 | Jewett . |
| 3,995,628 | 12/1976 | Gula et al. . |
| 4,160,451 | 7/1979 | Chittenden . |
| 4,342,313 | 8/1982 | Chittenden . |
| 4,397,091 | 8/1983 | Gustavsson et al. . |
| 4,568,334 | 2/1986 | Lynn . |

(List continued on next page.)

FOREIGN PATENT DOCUMENTS

| 1213571 | * | 3/1966 | (DE) | 128/658 |
| 4193252 | * | 7/1992 | (JP) | 128/657 |
| WO 9320876 | | 10/1993 | (WO) . | |
| WO 9416762 | | 8/1994 | (WO) . | |

*Primary Examiner*—Sharon Kennedy
*Assistant Examiner*—Catherine Serke
(74) *Attorney, Agent, or Firm*—Sterne, Kessler, Goldstein & Fox PLLC

(57) ABSTRACT

A method and apparatus are provided for releasably storing the additional exchange length of a medical guidewire within a housing, in a compacted configuration until it is needed by the physician to perform a catheter exchange. This guidewire has a distal portion which is similar to a traditional guidewire in length and construction and is used throughout the catheterization procedure much like a conventional guidewire. A proximal portion of the guidewire provides added length to effect a catheter exchange in the manner of a conventional exchange wire but may be tightly compacted and stored out of the way within a storage receptacle until the moment that the added length is needed for an exchange. The storage receptacle enables the physician to utilize the distal portion of the guidewire wire much like a conventional guidewire, then release the proximal portion quickly to effect a catheter exchange. The readily available additional length of wire offers the physician all the advantages of a traditional exchange wire while avoiding the handling problems associated with an uncontained exchange length that is unneeded during much of the procedure. The guidewire wire containment system of the present invention simplifies catheterization procedures by enabling the physician to maintain wire position during an exchange while keeping the exchange length of wire conveniently contained until it is needed to complete the procedure.

20 Claims, 16 Drawing Sheets

U.S. PATENT DOCUMENTS

| | | | | |
|---|---|---|---|---|
| 4,655,750 | | 4/1987 | Vaillancourt . | |
| 4,664,113 | * | 5/1987 | Frisbie et al. | 128/657 |
| 4,713,059 | | 12/1987 | Bickelhaupt et al. . | |
| 4,860,742 | | 8/1989 | Park et al. . | |
| 4,860,757 | | 8/1989 | Lynch et al. . | |
| 4,903,826 | * | 2/1990 | Pearce | 206/409 |
| 4,917,094 | | 4/1990 | Lynch et al. . | |
| 4,944,740 | | 7/1990 | Buchbinder et al. . | |
| 4,957,117 | | 9/1990 | Wysham . | |
| 4,960,411 | | 10/1990 | Buchbinder . | |
| 4,976,697 | | 12/1990 | Walder et al. . | |
| 5,064,415 | | 11/1991 | Walder et al. . | |
| 5,114,414 | | 5/1992 | Buchbinder . | |
| 5,117,838 | | 6/1992 | Palmer et al. . | |
| 5,117,839 | | 6/1992 | Dance . | |
| 5,125,416 | | 6/1992 | Phillips . | |
| 5,125,906 | | 6/1992 | Fleck . | |
| 5,133,364 | | 7/1992 | Palermo et al. . | |
| 5,163,927 | | 11/1992 | Woker et al. . | |
| 5,185,004 | * | 2/1993 | Lashinsky | 128/657 |
| 5,192,295 | | 3/1993 | Danforth et al. . | |
| 5,209,730 | | 5/1993 | Sullivan . | |
| 5,219,332 | * | 6/1993 | Nelson et al. | 128/657 |
| 5,243,996 | | 9/1993 | Hall . | |
| 5,279,573 | * | 1/1994 | Klosterman . | |
| 5,282,478 | | 2/1994 | Fleischhaker, Jr. et al. . | |
| 5,325,868 | | 7/1994 | Kimmelstiel . | |
| 5,339,833 | | 8/1994 | Berthiaume et al. . | |
| 5,346,498 | | 9/1994 | Greelis et al. . | |
| 5,358,478 | * | 10/1994 | Thompson et al. | 604/95 |
| 5,364,355 | | 11/1994 | Alden et al. . | |
| 5,365,943 | | 11/1994 | Jansen . | |
| 5,366,444 | | 11/1994 | Martin . | |
| 5,421,348 | | 6/1995 | Larnard . | |
| 5,423,331 | | 6/1995 | Wysham . | |
| 5,443,081 | | 8/1995 | Klosterman . | |
| 5,462,527 | * | 10/1995 | Stevens-Wright et al. | 604/95 |
| 5,568,865 | * | 10/1996 | Mase et al. | 206/363 |
| 5,641,067 | * | 6/1997 | Ellis | 206/409 |
| 5,642,736 | * | 7/1997 | Avitall | 128/772 |
| 5,666,968 | | 9/1997 | Imran . | |
| 5,707,376 | | 1/1998 | Kavteladze et al. . | |

* cited by examiner

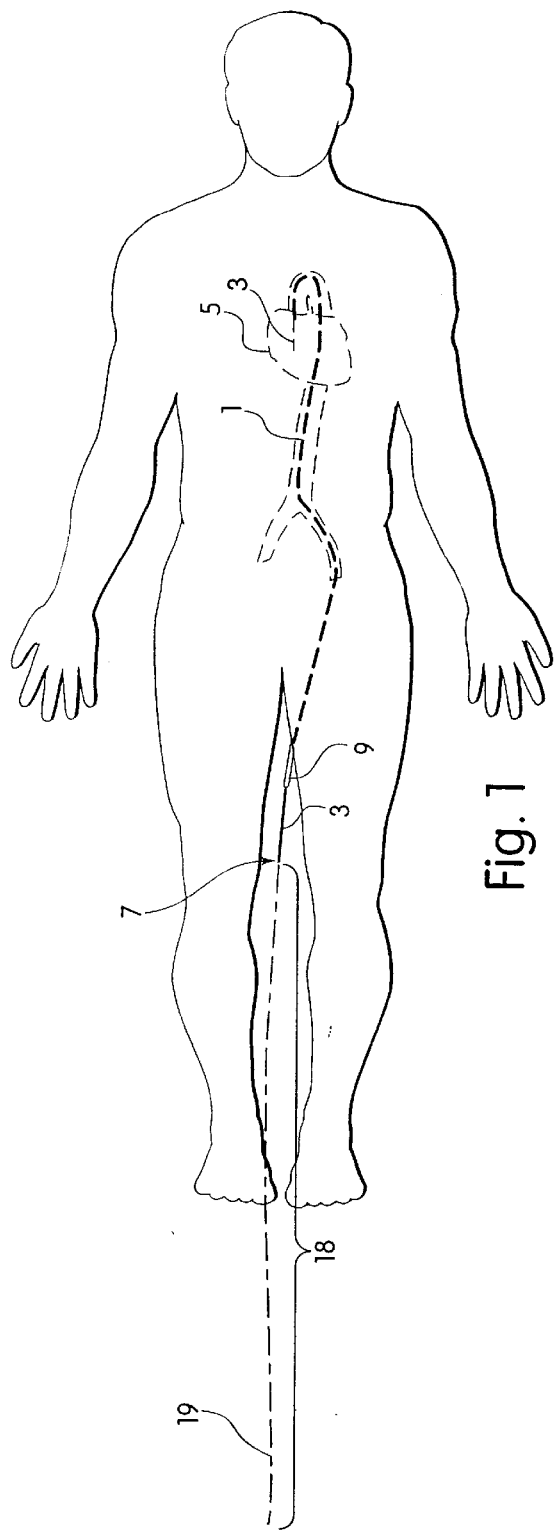
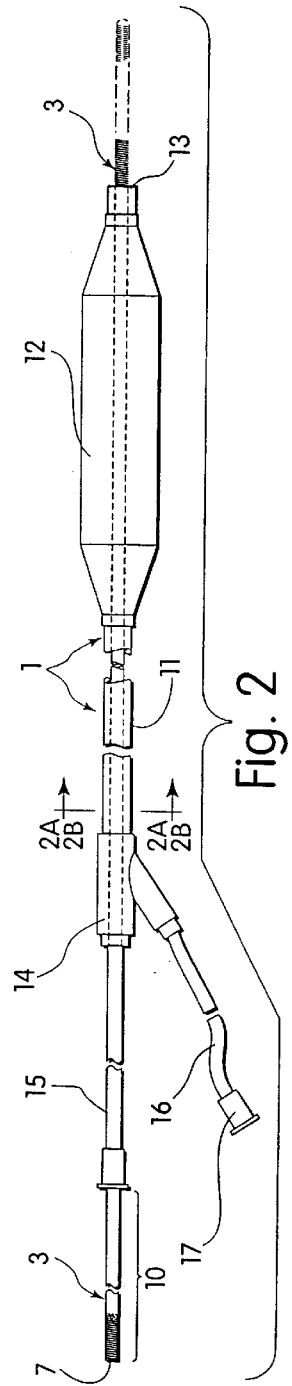
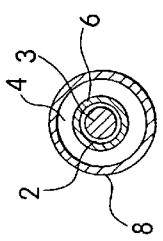
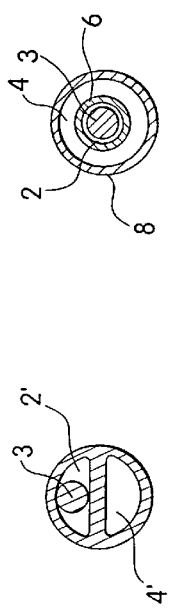

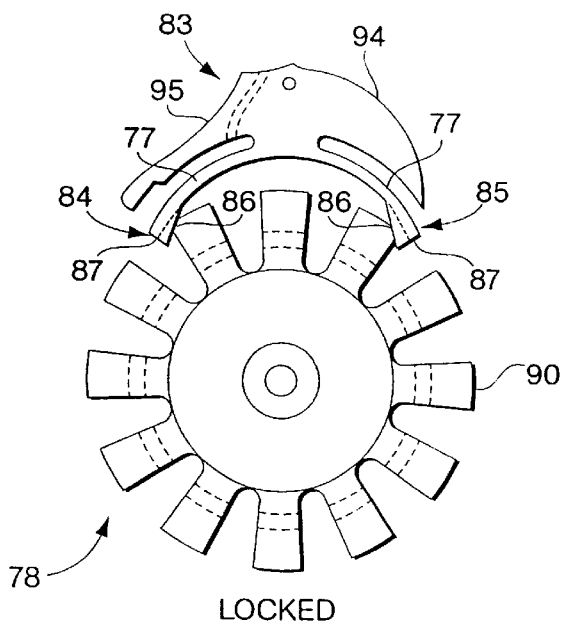
Fig. 16E LOCKED
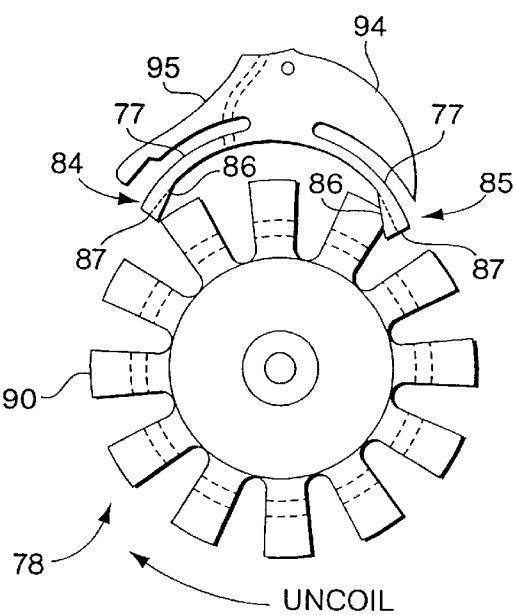
Fig. 16F UNCOIL
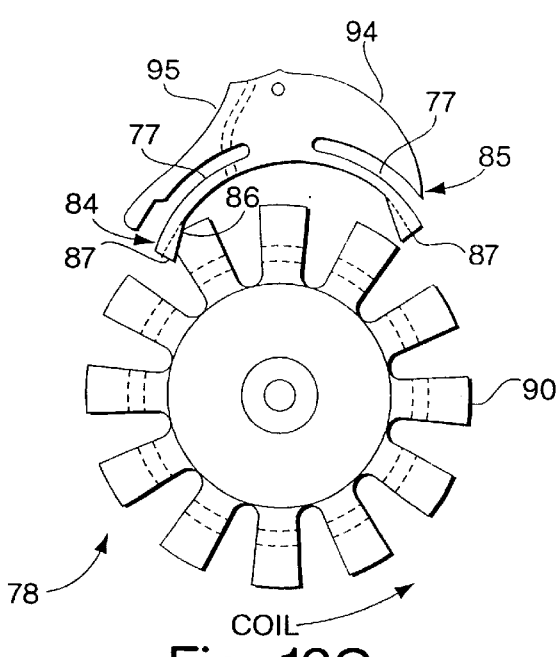
Fig. 16G COIL

STORABLE GUIDEWIRE SYSTEM

FIELD OF THE INVENTION

This invention relates to medical guidewires, extension wires and exchange wires and to improved methods and devices to facilitate procedures involving their use.

BACKGROUND OF THE INVENTION

A wide variety of medical catheterization procedures involve the cooperative use of a guidewire over which the catheter can be threaded so that the guidewire can guide the catheter to the intended site in the patient's body. The use of a guidewire reduces the risk of trauma to the patient by the advancing catheter and enables the catheter to be advanced quickly, thereby reducing the time required for the procedure. The guidewire typically is more easily manipulated by the physician into a desired position in the patient's body than is the far more flexible catheter. After the guidewire has been directed to the desired location in the body, the catheter then can be threaded over and along the guidewire, with the wire providing support and guidance for the flexible catheter.

Guidewires are used frequently in connection with catheters adapted for the diagnosis or treatment of the cardiovascular system. They are useful particularly in connection with those procedures where it may be necessary for the physician to use a series of different catheters that are inserted into and withdrawn from the patient. Each of the catheters may be provided with a different shape, size, configuration or implement suited for a specific purpose. For example, angiographic studies typically include the use of at least three cardiac catheters including a right coronary artery catheter, a left coronary artery catheter and a pigtail catheter. Each has a different shape and configuration at its distal end (the end inserted into the patient; the opposite end, is the "proximal" end), each being designed to facilitate placement of the distal end of the catheter at specific locations within the region of the heart. By way of further example, other types of catheters may include balloon dilatation catheters intended to be placed within an obstructed (stenosed) portion of an artery and then inflated under high pressure to expand the lumen of the artery and improve blood flow through the artery. Such a dilatation procedure is commonly referred to as "angioplasty" and has had significantly increased use for nearly two decades in the treatment of coronary artery disease. Still other types of catheters, such as atherectomy catheters, catheters incorporating optical elements for the transmission of light, catheters used in the delivery of a stent, among others, often are used in connection with guidewires.

It is common in the use of wire guided catheters for the physician to withdraw the catheter from the patient and substitute another catheter in its place. When doing so, it is desirable to leave the guidewire in place in order that the guidewire can be used to advance the succeeding catheter directly to the treatment site with a minimum of delay and trauma. In order to maintain the guidewire in place while withdrawing the catheter, the guidewire must be held in its position in the blood vessel as the catheter is withdrawn. The catheter, however, typically is longer than the proximal portion of the guidewire that protrudes out of the patient. Thus, before the catheter is fully withdrawn it completely covers the proximally extending end of the guidewire such that the physician can no longer grasp the guidewire. In order to effectively remove the catheter while permitting the guidewire to remain in place, some means must be provided to prevent the guidewire from being dragged out of position as the catheter is removed. This problem is frequently encountered in coronary angioplasty procedures and, therefore, the present invention, and its background, will be described in the context of a percutaneous trans luminal coronary angioplasty (PTCA) system.

Dilatation catheters commonly used in PTCA include an elongate flexible shaft of the order of about 150 cm long having a dilatation balloon mounted to the distal end of the shaft and an inflation lumen extending longitudinally within the shaft from the proximal end to the interior of the balloon so that the balloon may be inflated and deflated. Often such PTCA catheters also are provided with a full length guidewire lumen that receives a guidewire and terminates in openings at the distal tip of the shaft and at the proximal end of the catheter. When the guidewire and catheter are placed within a patient's artery, the guidewire can be manipulated and navigated to a desired location. The catheter then can be advanced, guided by the guidewire, to that location.

Typically, the balloon dilatation catheter and guidewire are guided to the entrance of one of the coronary arteries through another previously placed, larger diameter, single lumen catheter (a guide catheter). The guide catheter commonly is percutaneously inserted into the patient's femoral artery and is advanced along the aorta toward the heart. The guide catheter typically is provided with a pre-shaped distal tip adapted to engage and remain at the coronary ostium leading to the coronary artery. Once positioned, the guide catheter remains in place throughout the procedure to provide direct, quick access to the entrance of the coronary artery.

It is common during a PTCA procedure for the physician to exchange the balloon catheter for another catheter. This may occur if the physician initially performed a partial dilatation with a small diameter balloon and then wished to further dilate the patient's artery by using a catheter having a larger balloon. Catheters may also be exchanged to perform further operations in the artery such as stent placement or other treatment. Several techniques are commonly used to exchange a catheter, all designed to enable withdrawal of the catheter without losing guidewire position.

Among the techniques for effecting a catheter exchange is one in which the conventional guidewire (approximately 175–190 cm long) is removed from the indwelling balloon catheter and is replaced with a longer exchange wire, usually about 300 cm long. The additional length of the exchange wire results in a long proximally protruding portion that is longer than the catheter to be withdrawn. When the balloon catheter is withdrawn, some part of the proximally extending portion of the exchange wire will always be exposed to provide a means by which the exchange wire can be grasped and its position in the blood vessel maintained. After the 300 cm exchange wire has replaced the conventional length guidewire, the original catheter then is withdrawn over the exchange wire, which is grasped and held in place by an assistant. The next succeeding catheter then can be inserted into the patient over the exchange wire. The exchange wire provides a direct path to guide the new catheter to the portion of the blood vessel to be treated. If desired, the exchange wire then may be removed and replaced with a conventional length guidewire, although some physicians may prefer to permit the exchange wire to remain in place for the remainder of the procedure, especially if additional catheter exchanges are contemplated.

The technique of using a long exchange wire is not free from difficulty. The proximally extending end of the exchange wire is quite long and cannot be manipulated easily, should it be desired to do so. Typically, the use of a long exchange wire requires removal of the original standard length guidewire and replacement with the exchange wire. An assistant must hold the proximal end of the exchange wire at all times so that it does not fall to the floor, become kinked or contaminated. The placement of the exchange wire is performed under fluoroscopy to assure that it is properly placed in the patient's blood vessel. The use of a separate exchange wire also adds to the time and complexity of the procedure.

Another technique omits the necessity for an exchange wire by providing a guidewire extension that is attached to the proximal end of the conventional length indwelling guidewire, thereby effectively extending the length of the portion of the guidewire that protrudes out of the patient. The guidewire length is extended sufficiently to permit the catheter to be withdrawn and a new catheter to be threaded back into the patient without losing guidewire position. U.S. Pat. No. 4,917,103 discloses an illustrative guidewire extension system.

It would be desirable to provide a simple, effective and inexpensive system and technique for providing an extended length guidewire to enable withdrawal of an indwelling over-the-wire catheter while leaving the guidewire in place and to provide a system to facilitate catheter exchanges. It is the general object of the present invention to provide such a system.

SUMMARY OF THE INVENTION

The present invention provides an improved method and apparatus for performing a catheter exchange using a guidewire. This invention enables a physician to carry out a catheter exchange while maintaining guidewire position within the patient. The guidewire of the present invention has a distal guidewire portion of approximately 145 centimeters in length and a flexible proximal extension portion of approximately 155 centimeters in length, yet avoids the handling difficulties usually associated with a 300 centimeter length exchange wire. The long guidewire of the present invention is more manageable because the proximal extension portion, that provides the additional length needed for an exchange, may be gathered up and retained in a compact form capable of being held within the hand of the user until it is needed for an exchange. Though the added length of conventional exchange wires can be cumbersome to handle, the compactable wire of the present invention allows the physician to control the wire easily during the procedure. In catheterization procedures where time and simplicity of operation are important to the physician, the guidewire and method of the present invention are a significant improvement in catheter exchange performance.

The distal portion of the guidewire is approximately 145 centimeters long and is similar to a conventional guidewire and in that it and may be fabricated from a torsionally rigid material such as stainless steel. The proximal portion extends the length of the device approximately 155 centimeters and is connected to the distal segment by a connector. The connection may be permanent or releasable. If the connection is permanent, the two segments together operate similar to a conventional 300 centimeter exchange wire. The material used for the proximal extension segment may be more flexible and elastic than that of the distal guidewire segment. The proximal segment may be fabricated from a superelastic alloy of titanium and nickel (nitinol). Such a material will allow the extension portion of the wire to be tightly gathered in a compact configuration (e.g., coiling), yet avoid permanent deformation. Therefore, the added length for exchange provided by the extension portion may be easily maintained out of the physician's way until it is needed, at which point it can be released and returned to a relatively straight configuration for an over-the-wire catheter exchange. The less elastic distal guidewire portion of the wire is not intended to be coiled and stowed away as it will be used as a conventional guidewire, inserted in the patient during the catheterization.

The invention may be practiced with a variety of storage receptacles to hold the extension portion of the wire in a compact configuration until it is needed for a catheter exchange. The storage receptacle may be configured as a housing capable of releasably retaining the proximal extension portion of the guidewire in a compacted configuration within its interior. One type of housing is a disposable shell that can be quickly split away from the compacted proximal portion of the wire. This type of housing is intended for one-time use. The shell may be molded or heat sealed around the compacted extension portion during manufacture. The shell may be removable by a pull tab or a snap, tearing away completely from the extension portion of the wire. Upon release from the housing, the proximal portion of the wire assumes its straight configuration, in readiness for a catheter exchange. Once used, the split shell is spent and cannot be reused to recoil and store the wire. To facilitate use after the exchange, the physician may disconnect the extension portion from the indwelling guidewire portion of the wire if the connection is releasable. If the connection is permanent, the physician may wish to cut off the proximal portion or simply leave the full length intact for the remainder of the procedure.

Before the housing is removed it may serve as a steering handle for the distal guidewire portion. The coil of wire provides a handle through which torque may be transmitted to the straight distal portion of the wire. The size and shape of the shell housing surrounding the coil are suitable to enable it to be gripped and manipulated as needed to maneuver the wire through the patient's vasculature.

Not infrequently during a catheterization procedure, multiple exchanges are contemplated. To accommodate the possibility of multiple exchanges, several embodiments of the housing may be reused to recapture the proximal extension portion of the wire after a first exchange and store it in readiness for future exchanges. One embodiment of this type of housing has a hollow proximal storage portion having interior surfaces shaped to receive and direct the wire into a coil. The formed coil may lie approximately in a plane that is generally perpendicular to the axis of the straight wire portion. The proximal storage end of the housing transitions into a neck shaped to guide the wire out of the housing as it uncoils. The coil of wire retained within the housing may be of a diameter as small as twenty times the wire diameter.

While the wire is coiled inside the housing, a clamp may be locked around the wire enabling the housing to be used as a steering handle to navigate the distal guidewire portion through the patient's blood vessels. The clamp may be located on the neck of the housing and engaged to prevent movement of the wire with respect to the housing. To release the coiled wire to its exchange length, the physician loosens the clamp then pulls back on the housing while manually feeding the wire out through an access port at the end of the neck. When the wire is fully withdrawn from the housing a catheter exchange may be performed. After the exchange, the proximal portion of the wire may be returned to its coiled configuration in the housing by manually feeding the proximal end of the wire back through the access port into the neck of the housing. As the wire enters the hollow proximal portion of the housing, it encounters and is guided by the internal surfaces of the housing which cause the wire to resiliently assume the coil shape.

Another embodiment of the wire housing provides for a rotatable storage reel within the housing on which the extension portion of the wire can be wound. The wire is coiled upon a reel, rotatably contained within the housing. When an exchange is desired, the coiled wire is withdrawn manually from the unwinding reel of the housing. To return the wire to the housing for storage in a coiled configuration, the proximal end of the wire is reinserted into the access port of the housing. As it is fed inward, the wire becomes engaged by the reel which then can be rotated to draw the remainder of the extension portion of the wire back to a coiled form.

The storage receptacle may also be an open device upon which the wire is wound for storage. The open receptacle may be shaped as a spool having a perimeter surface shaped to retain the wire wrapped around the surface. The spool may be grasped directly by the operator to manually wind an extended wire around its perimeter or the spool may rotate freely about an axle to quickly unwind a stored wire. The spool may have catch members around its perimeter surface to prevent the wire from springing off the spool once it has been wound.

It is among the general objects of this invention to provide an improved guidewire, storage system and method that will facilitate an over-the-wire catheter exchange while maintaining wire position within the patient.

It is another object of the invention to provide a guidewire having a distal guidewire portion and a proximal extension portion that is more resilient and flexible than the distal portion such that it may be stored in a compact configuration within a small receptacle without adverse permanent deformation.

A further object of the invention is to provide a receptacle that is an easily removable shell housing to retain the compacted portion of the guidewire.

Still another object of the invention is to provide a housing that enables the user to return the proximal extension portion of the guidewire to its compacted form within the housing after having been extended to perform a catheter exchange.

Still a further object of the invention is to provide a method of catheter exchange using the type of guidewire described where the proximal portion of the wire remains stored in a compacted form within a housing until it is ready to be used by the physician for an exchange.

Another object of the invention is to provide devices and techniques of the type described that are inexpensive and simple to make and use.

DESCRIPTION OF THE DRAWINGS

The foregoing and other objects and advantages of the invention will be appreciated more fully from the following further description thereof, with reference to the accompanying drawings wherein:

FIG. 1 is a diagrammatic illustration of a patient undergoing coronary catheterization.

FIG. 2 is a somewhat diagrammatic, fragmented illustration of a conventional over-the-wire catheter and guidewire.

FIG. 2A is a cross-sectional illustration of a two-lumen extruded type of catheter shaft as seen along the line 2A—2A of FIG. 2.

FIG. 2B is a sectional illustration of a two-lumen, two-tube coaxial type of catheter shaft as seen along the line 2B—2B of FIG. 2.

FIG. 16E is an illustration of both pawls engaging the storage reel, preventing rotation in either direction.

FIG. 16F is an illustration of the uncoil pawl engaging the storage reel, preventing rotation in the coil direction.

FIG. 16G is an illustration of the coil pawl engaging the storage reel, preventing rotation in the uncoil direction.

DESCRIPTION OF THE ILLUSTRATIVE EMBODIMENTS

Figure 3:
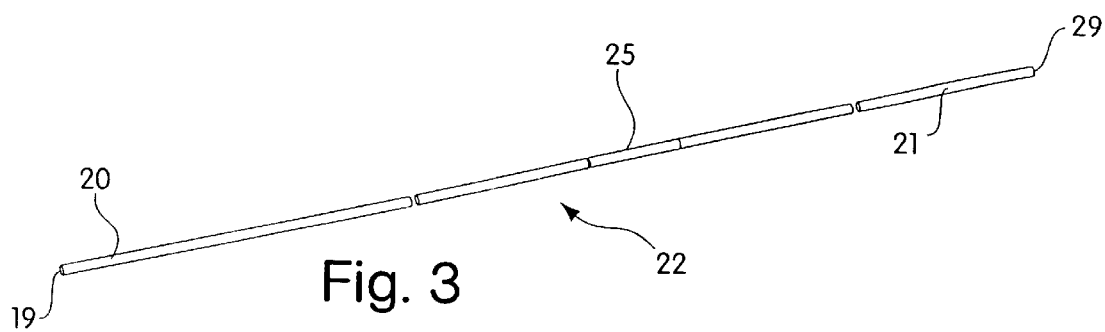
FIG. 3 is a diagram of a segment of the guidewire of the present invention depicting the distal portion of the wire in a straight configuration, the proximal extension portion of the wire in its undeformed straight configuration and a connector joining the portions.

FIG. 1 illustrates, in highly diagrammatic form, a catheter 1 and guidewire 3 which have been inserted into a patient's femoral artery and have been advanced to the region of the patient's heart 5 where a desired procedure will be performed. The guidewire 3 and catheter 1 will have been inserted and placed in the artery in accordance with well known procedures typically including the preliminary placement of a single lumen guide catheter (not shown in FIG. 1).

When it is desired to exchange the indwelling catheter 1 for another, it is important that the guidewire 3 be maintained in its position within the patient's artery so that it may guide the next succeeding catheter quickly and efficiently to the intended site in the patient's vascular system. Typically, the clearances between the guidewire 3 and inner lumen of the catheter 1, coupled with the bends which the catheter and guidewire must follow along the patient's vascular system, are such that withdrawal of the catheter 1 tends to drag the guidewire out with the catheter 1. In order to maintain the guidewire in place while the catheter 1 is withdrawn, it is necessary to hold the indwelling guidewire 3 by its proximal end 7 while withdrawing the catheter 1 over the guidewire 3. That has presented some difficulty because the proximal end 7 of a conventional guidewire only protrudes beyond the proximal end 9 of the catheter by an amount that is substantially less than the length of the catheter 1. Therefore, it has been necessary to resort to use of the systems and techniques discussed above, among others, in order to perform a catheter exchange.

FIG. 2 illustrates the proximal (at the left) and distal (at the right) ends of a conventional over-the-wire catheter with the ends of the guidewire 3 protruding out of the corresponding ends of the catheter 1. The illustrated catheter 1 includes an elongate, flexible shaft 11, formed with two lumens 2', 4' (FIG. 2A) or 2, 4 (FIG. 2B) extending through the shaft, one of the lumens 2 or 2' extending fully through the length of the shaft to receive a guidewire 3 and the other lumen 4 or 4' communicating between the proximal end of the catheter and a dilatation balloon 12 mounted at the distal end of the catheter. The distal end of the guidewire lumen 2 or 2' terminates in an outlet orifice 13 through which the distal end of the guidewire 3 protrudes. The inflation lumen 4 or 4' terminates within the balloon 12 and serves to communicate inflation medium (typically a radiopaque liquid) to and from the balloon 12 to effect inflation or deflation. The catheter shaft 11 may be formed from a variety of conventional polymers used to form catheter shafts such as polyethylene and nylon, among others. The catheter shaft 11 may be of any conventional construction such as, for example, an extruded two lumen shaft (FIG. 2A) or a pair of coaxial tubes 6, 8 (FIG. 2B) in which the inner tube defines the guidewire lumen 2. The material from which the catheter shaft is formed and which defines the guidewire lumen, should have sufficiently low frictional characteristics so as to cooperate with the guidewire to enable the catheter shaft to easily slide over the guidewire. The outer surface of the guidewire 3 may be coated with a material to enhance its lubricity, such as Teflon, hydrophilic material or other materials commonly used for such purpose.

The proximal end of the catheter includes a bifurcate fitting 14 which joins a guidewire leg 15 and an inflation leg 16 to the catheter shaft 11 to communicate, respectively, with the guidewire and inflation lumens 2, 4. The inflation leg 16 has a fitting 17 at its proximal end that may be connected to a source of pressurized inflation medium. A similar connector fitting may be attached to the proximal end of the guidewire leg 15.

The operation and function of a conventional over-the-wire catheter and guidewire is well known to those familiar with the art. Should it be desired to effect a catheter exchange, one common approach is to use an extension wire that can be attached to the proximal end of the guidewire so that the combined overall length of the guidewire and extension wire (not shown) may be of the order of 300 to 400 cm long. The additional effective length, as compared to the conventional guidewire length is represented by the phantom line 18 in FIG. 1. The length of the extended guidewire is such that its proximal end 10 is spaced from the proximal end of the guide catheter by a distance that is greater than the length of the operating (dilatation) catheter. Consequently, a portion of the guidewire or extension always is exposed and can be grasped by the physician to maintain the position of the guidewire as the catheter exchange is performed. Such a guidewire extension system is disclosed, for example, in U.S. Pat. No. 4,917,103 issued Apr. 17, 1990.

The guidewire 22 of the present invention is shown in FIG. 3. The wire has a proximal end 29 and a distal end 19. The wire has a distal portion 20 that is approximately 145 cm long that may embody a conventional PTCA guidewire structure and a more elastic proximal extension portion 21 approximately 155 cm long. The two wire portions are connected together, permanently or releasably, by such means as a hypotube connector 25 of the type routinely used in extension wire systems. Illustrations of such a guidewire-to-extension wire connection may be found in U.S. Pat. No. 5,133,364 (Palermo et al.), the disclosure of which is hereby incorporated by reference herein, in its entirety and in U.S. Pat. No. 4,827,941 (Taylor et al.) and U.S. Pat. No. 5,113,872 (Jahrmarkt et al.). In FIG. 3, connector element 25 is meant to suggest the Palermo device.

Figure 4:
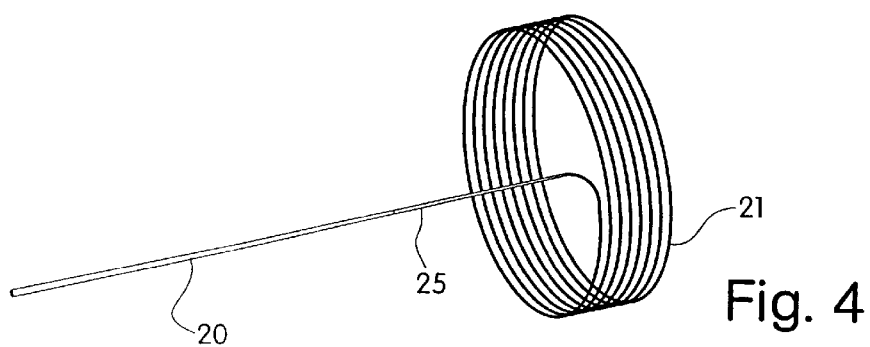
FIG. 4 is an illustration of the distal portion of the wire in a straight configuration and the proximal extension portion of the wire in a coiled configuration and the connector.

The distal guidewire portion 20 of the guidewire may be constructed in any of a number of configurations known in the art. For example, for use in percutaneous transluminal coronary angioplasty, it may be desirable to embody a steerable guidewire construction such as that disclosed in U.S. Pat. No. 4,545,390 (Leary). Such steerable guidewire is characterized by an elongate flexible shaft, typically formed from metal, such as stainless steel, that while longitudinally flexible also displays sufficient torsional rigidity so that rotation applied to the proximal end of the guidewire is transmitted controllably to the distal end that protrudes out of the distal end of the catheter. Although the guidewire is longitudinally flexible, it nevertheless is stiffer than the angioplasty catheter with which it is used. Guidewires used in coronary angioplasty commonly have a shaft of a diameter of between about 0.012 to about 0.018 inches diameter, with 0.014 inch diameter being most commonly used. Other guidewire constructions particularly suited to the intended procedure, of course, may be employed for the distal portion, so long as a proximal portion 21 of the guidewire is made of a more elastic material that avoids adverse permanent deformation. As described in further detail below, the proximal extension portion 21 should be capable of returning to a substantially undeformed, straight, configuration after being constrained in a tightly gathered configuration such as the coil shown in FIG. 4.

The proximal extension portion 21 of the guidewire 22, having the desired elastic properties, may be formed from material having a lower modulus of elasticity than the distal portion of the wire. The wire should be capable of returning to a straight configuration after release from storage to enable the over-the-wire catheter to be exchanged. A suitable material for the wire is considered to be the superelastic form of nitinol, a titanium-nickel alloy which has a modulus of elasticity of the order of 8,000,000 p.s.i., as compared to about 29,000,000 p.s.i. for stainless steel. Nitinol wire can be coiled tightly for storage yet return to an undeformed, straight configuration immediately upon release. A range of other materials also may be suitable for the proximal extension portion as long as they result in no permanent deformation and allow for manual loading of the wire into a storage housing. Other possibilities include: thin wires of material other than nitinol, arranged in a braid or close pitched spring having an inner core wire; plastic jacketed single filament wire; stiff plastic; or reinforced plastic.

One embodiment of a receptacle to retain the proximal extension portion of the wire in a compact configuration is a housing illustrated in FIGS. 5, 6, 7 and 7A. The housing may comprise a shell 23 that contains the proximal extension portion of the wire 21 in its coiled configuration until it is needed to complete an exchange procedure. The shell 23 may be formed around the coil by heat shrink wrapping plastic material around the coil. During shrink wrapping, the wire may be restrained in its coiled form around a light weight spool 28 or it may be held together by convenient temporary restraining means such as wire twist strips 27. By way of example, in this embodiment the wire may be in a coil that is of a diameter equal to approximately twenty times the wire diameter. A wire diameter of approximately 0.011 inch thus may have a shell approximately 0.22 inch in diameter and 0.2 inch thick.

Figure 6:
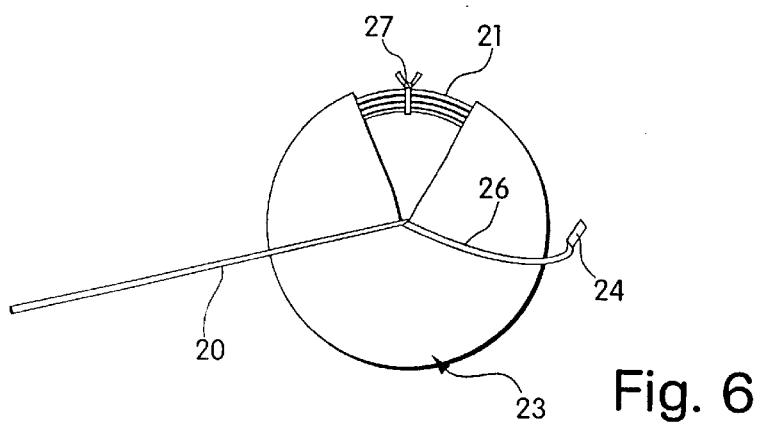
FIG. 6 is a front view of the shell housing of FIG. 5 being split away from the stored wire by a release tab.

A pull tab 24 may be incorporated into the shell to allow the shell to be peeled away, thereby releasing the coiled proximal extension. The pull tab 24 may be defined by the free end of a tear strip 26 of dissimilar material, adhered to or imbedded into the plastic material before it is sealed around the coil. Pulling the tear strip 26 will split the shell apart as is shown in FIG. 6 freeing the proximal portion of the wire 21 so that it can be returned to its straight, undeformed configuration. The spent shell may be discarded.

Figure 5:
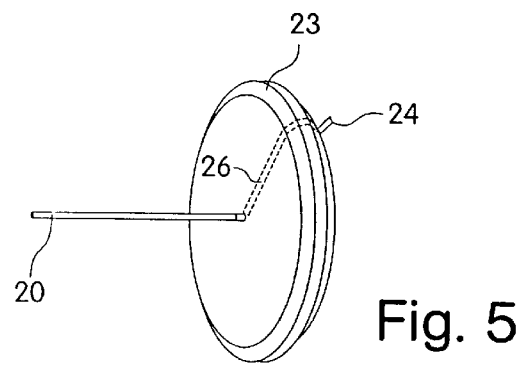
FIG. 5 is an isometric illustration of a frangible shell housing containing the proximal extension portion of the guidewire in a coiled configuration.
Figure 7:
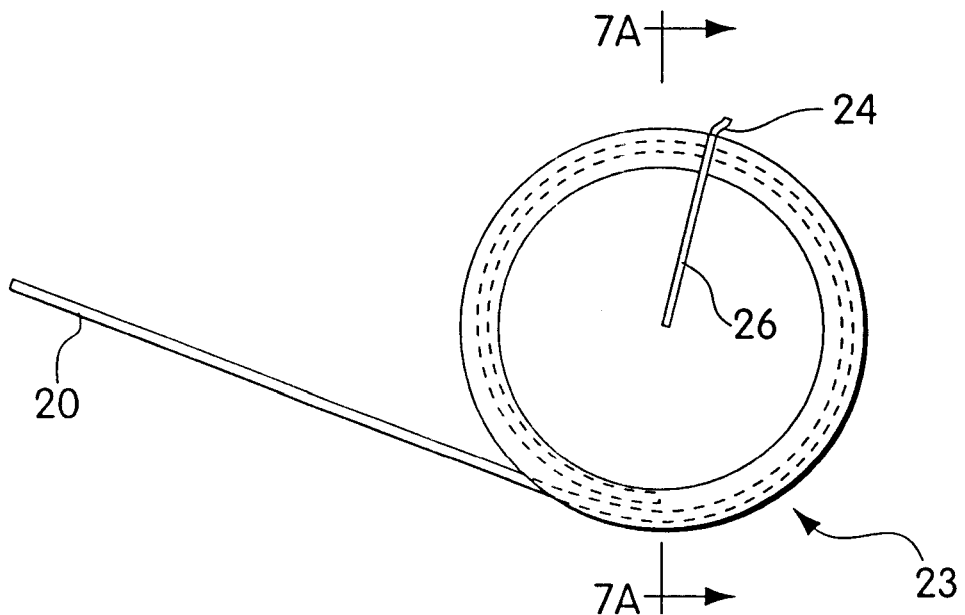
FIG. 7 is a side view of the shell housing containing a coil of wire in a plane which is parallel to the axis of the extending distal portion of the guidewire.
Figure 7A:
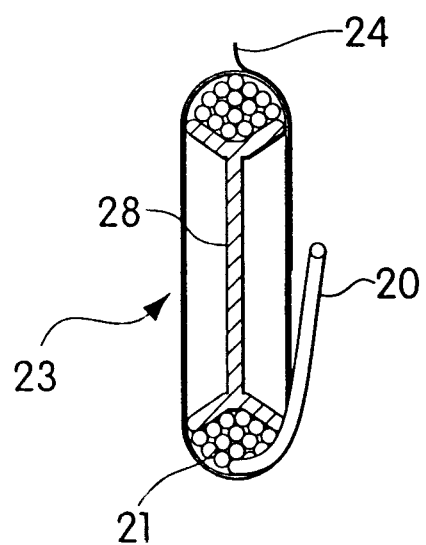
FIG. 7A is a sectional view of the shell housing containing the coil of wire around a lightweight spool in a plane which is parallel to the axis of the extending distal portion of the guidewire shown in FIG. 7 along the line 7A—7A.

Before the compact enclosed coil is released, the housing may be grasped conveniently to facilitate maneuvering the distal guidewire portion through the patient's blood vessels. Torque may be transmitted through the relatively rigid coil to the distal portion of the wire. The coil of wire may be retained by the shell 23 in a generally planar orientation that is perpendicular to the axis of the straight distal guidewire portion as shown in FIGS. 5 and 6 or parallel to the axis of the distal portion as shown in FIG. 7 and 7A.

Figure 8:
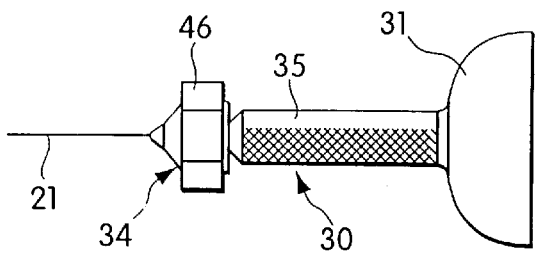
FIG. 8 is an illustration of the outside of a reusable housing capable of recapturing the extension portion of the wire.
Figure 9:
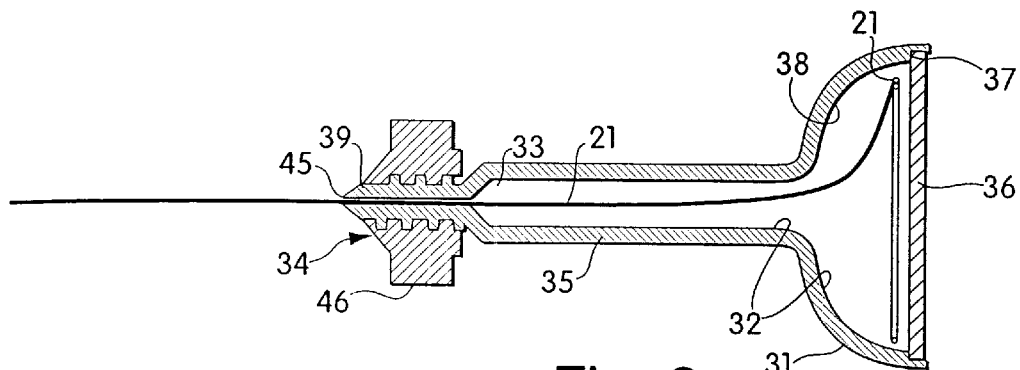
FIG. 9 is a longitudinal sectional illustration of the proximal extension portion of the guidewire disposed within the reusable housing.

Other embodiments may be provided in which a housing is reusable to recapture the wire and maintain it in a compacted configuration in readiness for a subsequent use. In one such embodiment, shown in FIG. 8, the user may manually withdraw the proximal portion of the wire 21 from its compacted form within a housing 30, perform a catheter exchange, then manually reinsert the wire back into the housing where it will be guided to its compacted form. The housing 30 is formed from a rigid material, preferably plastic. As shown in FIG. 9, the housing 30 has a hollow interior with surfaces 32 configured to direct an entering wire into a compact configuration such as a coil. The interior surfaces 32 may be somewhat conical, having a sidewall 38 that diverges from a neck 35 to a bottom wall 36 of the housing. The bottom wall 36 may be attached to the housing by ultrasonic welding or by an adhesive bond.

After an exchange, the wire may be recoiled by reinserting the proximal portion of the wire 21 into the access port 45 and advancing the wire into the housing 30. The wire passes through the bore 33 of the neck 35 and enters the housing 30 where it encounters the bottom wall 36, buckles, then springs outward radially in a coiled shape. As the insertion continues, the divergent sidewall 38 guides the wire to the inside corners 37 of the storage portion 31 of the housing 30 where the wire is contained in a coil.

The bottom wall 36 may be about one inch in diameter. The divergent sidewall may taper to a diameter of approximately 0.300" at the neck 35. These dimensions are intended to be illustrative only and the housing may be any size found to be preferred by the user, bearing in mind practical limitations. Housings larger than three inches in diameter may be too bulky to hold comfortably in one hand and housings smaller than 0.250" coil the wire so tightly that the increased reaction force, created by the wire's resiliency, makes the wire more difficult to load and unload.

Figure 10:
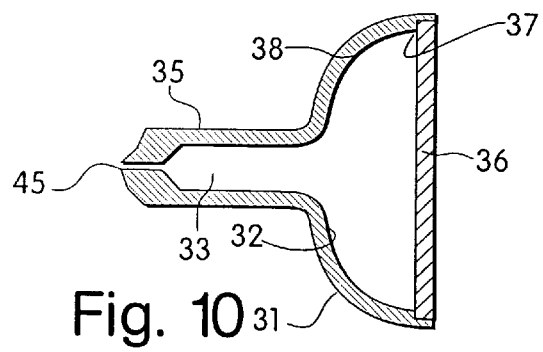
FIG. 10 is a sectional illustration of the reusable housing having a shortened neck.

The neck 35 of the housing is shaped to guide straightened wire to and from the interior of the housing 30 where the wire resides in a coiled configuration. During withdrawal, the wire uncoils within the cone area and then becomes essentially straight as it passes through the access port 45 and leaves the housing. The friction present between the wire 21 and the bore 33 of the neck 35 prevents the wire from suddenly springing out of the storage portion 31. The neck 35 may be elongated as shown in FIG. 9 or quite short in comparison to the length of the cone portion as is shown in FIG. 10. The neck 35 may have an outside diameter on the order of 0.300". A bore 33 through the neck is dimensioned to slidably receive the guidewire. A clamp 34 may be employed on the neck and may comprise an externally threaded collet 39 and cooperatively clamping nut 46.

Before the wire is uncoiled for an exchange procedure, the housing may be used as a handle to torque and manipulate the distal portion of the guidewire through the patient's vasculature. The housing may, but need not be, locked on to the wire by the clamp 34 as shown in FIGS. 8 and 9. Tightening the steering handle nut 46 around the collet 39 locks the wire within the bore 33 of the neck 35 of the housing to prevent movement of the wire with respect to the housing.

When the full length of the guidewire is needed for a catheter exchange, the clamp 34 is loosened and the housing 30 is withdrawn proximally of the wire. The indwelling catheter then can be withdrawn over the proximal extension portion 21 of the guidewire and a new catheter then can be loaded over the proximal extension portion of the guidewire and advanced into the patient. After the exchange, use of the guidewire distal portion 20 may be facilitated by removing the proximal extension portion 21 by cutting it off at the hypotube connector 25 or, if the connection is releasable, by disengaging. If another exchange is contemplated, the physician may leave the wire intact, continuing the procedure with the full length of the exchange wire uncoiled or the extension portion 21 may be reinserted into the housing 30. Once the proximal extension portion of the wire is reinserted, the nut 46 may be tightened around the collet 39 to lock the wire to the housing.

The clamp 34 can be secured to the extension portion 21 of the wire or to the hypotube connection 25 or to the proximal end of the distal guidewire portion 20 depending on the length of the neck 35. Clamping on the more elastic, proximal extension portion 21 will provide sufficient torque capability for maneuvering if the clamping point is near the hypotube connection 25 so that the length of extension portion that is subjected to torque is short. When clamping on the proximal extension portion of the wire, torque may be applied in only one direction to avoid disconnecting a hypotube connector of the type disclosed in U.S. Pat. No. 5,133,364 (Palermo et al.). Such connectors engage when the extension wire is rotated in one direction and disengage when rotated in the opposite direction. The proximal end of the distal guidewire portion 20 of the wire should not be inserted deeply into the housing 30 as it may be permanently deformed if it is coiled within the storage portion 31 of the housing.

Figure 11:
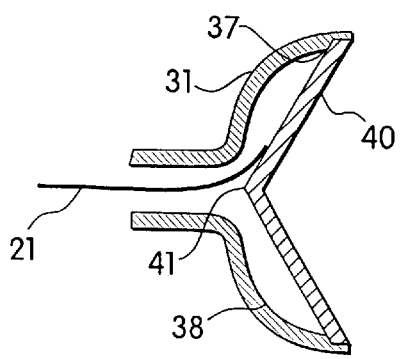
FIG. 11 is a sectional illustration of the proximal portion of a modified form of the housing having an interiorly convex bottom wall.

FIG. 11 shows the conical housing 30 having an interiorly convex shaped bottom 40 which serves to help direct the proximal extension portion of an entering wire 21 to the inside comers 37 of the cone for proper coiling. As the wire enters the storage region 31, it will first encounter the apex 41 of the end cap which deflects the wire radially outward toward the comer 37 of the housing. As the wire is inserted into the housing, it will continue to be guided into a coil at the inside comers 37.

Figure 12:
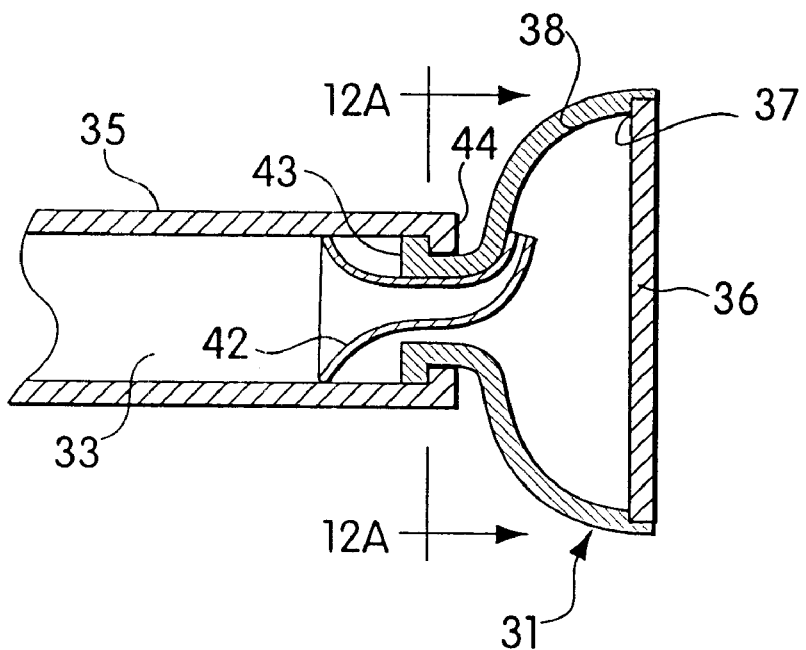
FIG. 12 is a sectional illustration of an embodiment of the reusable housing having a storage portion that is rotatable relative to the neck.
Figure 12A:
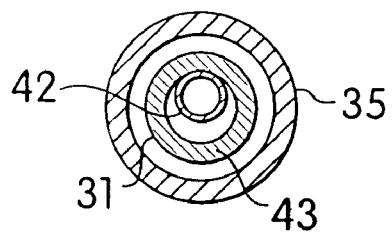
FIG. 12A is sectional illustration of the reusable housing having a storage portion that is rotatable relative to the neck shown in FIG. 12 along the line 12A—12A.

FIGS. 12 and 12A shows a modified embodiment of the housing in which the storage portion 31 is rotatable with respect to the neck 35. Enabling such relative rotation may reduce the risk of the wire becoming twisted as it uncoils and exits the housing. The storage portion 31 and neck 35 may be rotatably joined by the interlocking connection of an outwardly projecting lip 43 on the storage portion with an inwardly projecting shoulder 44 on the neck. In this embodiment a guide tube 42 may be provided to receive the proximal end of an entering wire in the neck of the housing and guide it, as it advances, to the storage portion 31. The guide tube prevents the wire from becoming caught on the lip 43 and shoulder 44 connection, guiding it instead along the divergent sidewall 38 of the storage portion so that it may become coiled along inside corners 37 of the cone. The guide tube 42 is attached to the interior surface 32 of the storage portion 31 and extends into the bore 33 of the neck 35. The distal end of the guide tube 42 is flared open to a diameter that is approximately equal to that of the bore 33 of the neck 35 to easily catch an incoming wire. The diameter of the tube decreases as the tube extends proximally into the storage portion to a size just large enough to slidably receive the guidewire. The guide tube may be joined to the interior surface 32 by conventional means such as adhesive and is positioned such that the centerlines of the tube and cone are eccentric. The tube terminates along the sidewall 38 of the cone, to direct the wire to the end corner 37 of the cone where it will become properly coiled. To help guide the end of the wire to the corner of the cone, the interiorly convex bottom discussed in connection with FIG. 11 may be employed in this housing embodiment.

Figure 13:
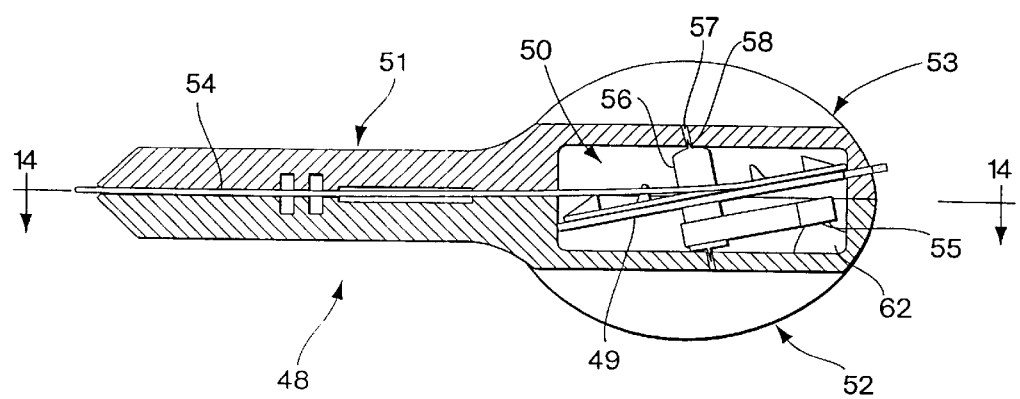
FIG. 13 is a side view of a housing that stores the wire on a wire storage reel that is rotated by an automatic return spring.
Figure 14:
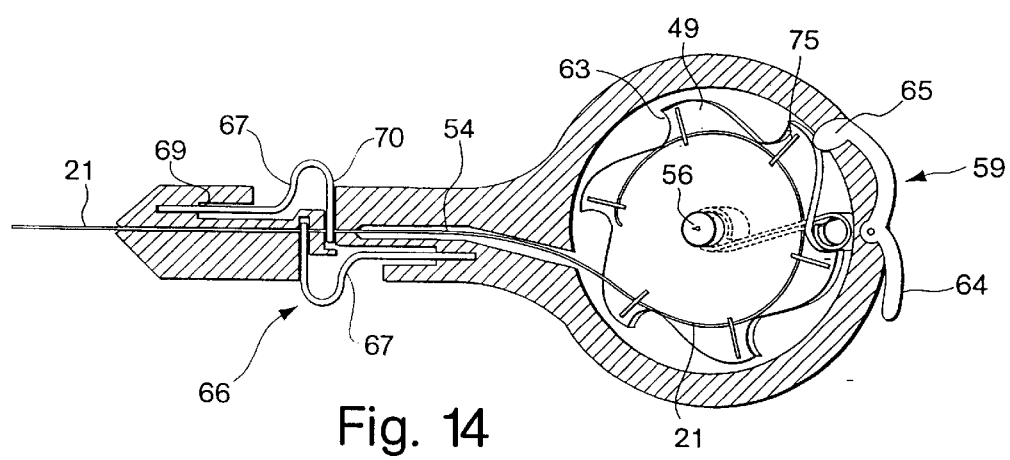
FIG. 14 is a sectional view of the housing of FIG. 13 along the line 14—14
Figure 15:
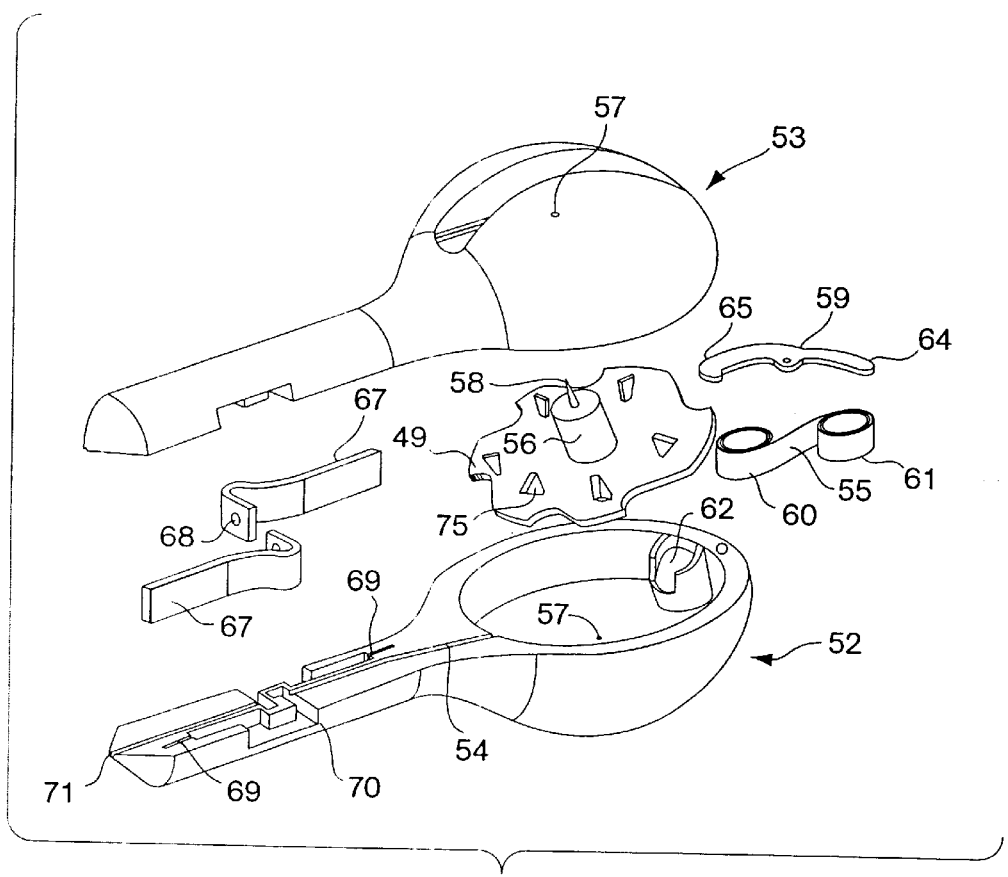
FIG. 15 is an exploded view of the housing depicting the wire storage reel, return spring, release lever, and wire brake system.

FIGS. 13–15 show another housing embodiment 48 in which the proximal extension portion 21 of the guidewire is wound in a coil on a rotatable storage reel 49 capable of retracting the wire into the housing manually or automatically under the influence of a return spring. The wire can uncoil from the reel and exit the housing through a bore 54 opening to an access port 71 in a neck portion 51 of the housing. FIG. 14 is a sectional view of the housing along line 14—14 showing the location of the coil of wire wrapped around the storage reel 49. The housing may be formed from an economical, lightweight, rigid material, such as plastic, that lends itself to disposable use. As shown in FIG. 15, the housing comprises a bottom half 52 and a top half 53 which are joined together during manufacture by conventional methods such as screws, adhesive or ultrasonic welding.

The reel 49 is rotatably located within the housing by an axle 58. The axle may be formed integrally with the hub 56 of the reel, rotating with the reel, or the axle may be a distinct piece, such as a stiff wire that remains fixed as the reel rotates around it. The ends of the axle 58 may be captured in molded projections or in holes 57 located in each half of the housing.

A fully extended guidewire that has been removed from the housing can be reinserted and recoiled automatically by torque provided by a return spring 55. A suitable return spring 55 is shown in FIGS. 14, 15, 15C and 16 and is available from the Vulcan Spring Mfg. Co. of Telford, Pa. It is a constant torque type made from a strip of thin rolled steel traveling between two spools. The spring is coiled upon itself into a storage spool 61 at one end, and at the other end, is wound reverse to its natural curvature into an output spool 60. When released, torque is obtained from the output spool 60 as the spring 55 returns to its natural curvature on the storage spool 61. The hub 56 of the storage reel 49 shown in FIGS. 13 and 14 is serves as an output spool so that as the reel rotates to uncoil the wire, the return spring spools onto the hub. When it is desired to recoil the wire by reversing the direction of rotation of the storage reel 49, the stored torque energy present in the output spool 60 which has been coiled onto the hub 56 of the reel will provide torque to rotate the reel until the spring becomes completely recoiled on the storage spool 61. The spring wound upon itself forming the storage spool 61 will be retained in a spring retainer recess 62 which is formed within the housing 48 adjacent to the wire storage reel 49. The constant torque provided by this spring throughout its travel between the spools creates a steady, moderate wire return speed into the housing. To avoid coiling and permanent deformation of the distal guidewire portion 20 of the wire, it is desirable to stop the wire's progress onto the return reel just before the hypotube connection 25 enters the housing. The reel can be made to stop at this predetermined point by designing the length of the return spring 55 to rotate the reel the correct amount of revolutions so that only the proximal extension portion 21 of the guidewire becomes coiled.

Automatic return of the wire onto the storage reel may be stopped by a release lever 59 that is pivotally mounted between its ends to the housing and engages the reel, holding it from rotating. The release lever has a handle end 64 that is operated by the user and a pawl end 65 which protrudes through the body of the housing and engages ratchet teeth 63 formed around the perimeter of the storage reel 49. When the pawl is engaging a tooth of the storage reel, the reel will not rotate in the direction of recoil. The ratchet teeth are shaped to allow the reel to slip by the pawl 65 when the reel is rotated in the uncoil direction. When the pawl 65 disengages the teeth, the reel 49 will be free to rotate under the force of the return spring, thereby automatically coiling the wire.

Figures 15A, 15B:
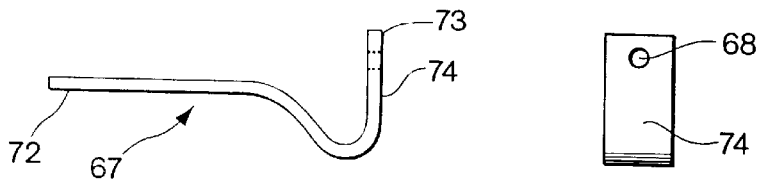
FIG. 15A is a side view of a cantilever spring used in the wire brake system.
FIG. 15B is a front view of a cantilever spring used in the wire brake system.
Figure 15C:
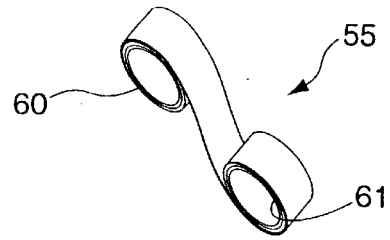
FIG. 15C is an illustration of the constant torque automatic return spring.
Figure 18:
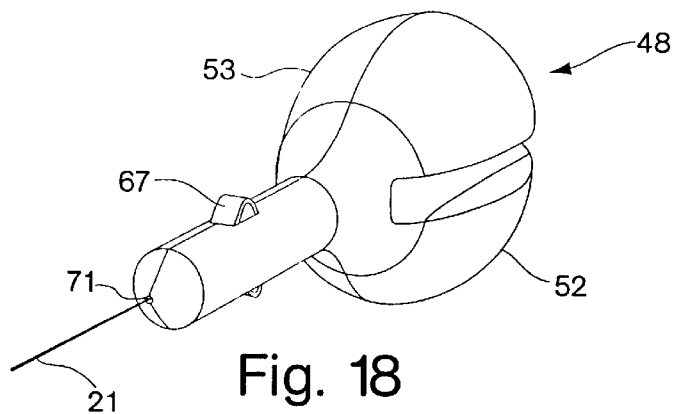
FIG. 18 is an illustration of a housing having a free-wheeling wire storage reel.

The housing may also include a wire braking system 66 mounted on the neck 51 of the housing to regulate the return speed of the wire onto the reel The brake may be any arrangement for frictionally engaging the wire to slow or stop its movement. The brake system shown in FIGS. 14, 15 and 18 is comprised of two cantilever springs 67 each having one fixed end 72 mounted in slots 69 that are formed directly into the housing body and a free end 73 having a flat portion 74 that may be substantially perpendicular to the fixed end 72 (see FIG. 15A). A hole 68, receptive to the guidewire, is drilled through the free end 73 of the spring. The springs are mounted in opposed relation to each other on the neck 51 of the housing with the fixed ends 72 extending parallel to each other along the neck and with the free ends 73 extending inward towards the axis of the neck 51. The free ends 73 are oriented in slots 70 with the holes 68 being biased in a misaligned configuration to the path of travel of the wire 21 through the neck. The springs must be flexed to align the holes to enable the wire to pass through the holes 68. When the springs are released, the friction between the wire and the misaligned holes restrains the wire from moving into or out of the housing. When the springs are pressed together to align the holes, the frictional drag on the wire is reduced to allow its movement into or out of the housing. The operator may regulate the return speed of the wire onto the storage reel 49 by increasing or decreasing force applied to the springs. The braking system also enables the user to maintain the wire stationary relative to the housing 48 so that steering forces may be applied to the housing and transmitted to the distal portion of the guidewire as it is maneuvered through the patient's vessels.

Figure 15D:
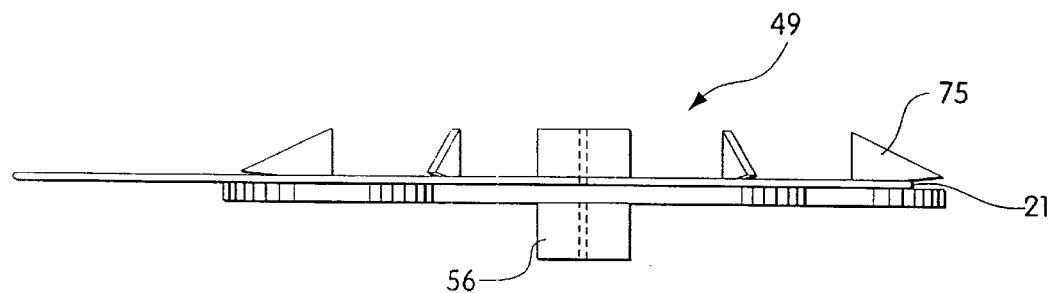
FIG. 15D is a side view of the storage reel having projections to locate the wire.
Figure 15E:
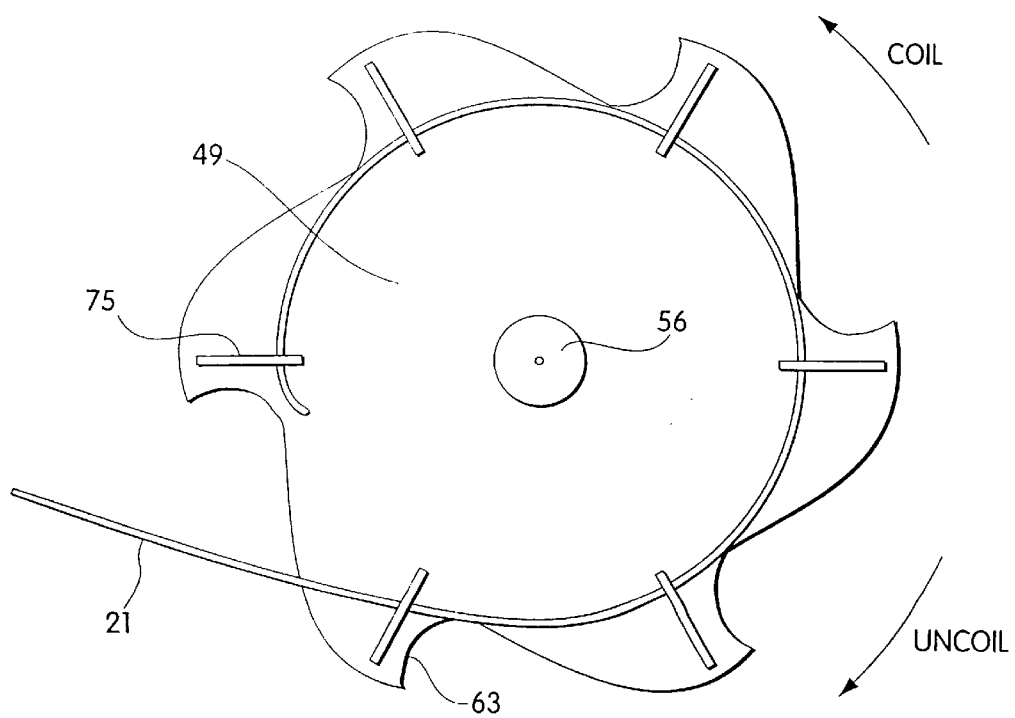
FIG. 15E is a top view of the storage reel having projections to locate the wire.

As shown in FIG. 14, the bore 54 of the neck 51 may be oriented to guide the wire to and from the perimeter of the reel 49 to facilitate engagement with the wire securing means on the storage reel. As shown in detail in FIGS. 15D and 15E the wire may be held onto the reel by several wedge shaped fingers 75 that project from the side of the reel 49, pointing radially outward around its perimeter. The wedge shape of the fingers causes the wire to become pinched between the converging surfaces of the side of the wedge and the sidewall of the reel, frictionally engaging it to prevent slippage. As reel rotates in the "coil" direction, the proximal end of the wire 21 projecting into the storage area 50 of the housing becomes trapped between the inside edge of the wedge shaped finger 75 and the surface of the reel. As the reel continues to rotate, wire will be continually drawn into the housing and snared on to succeeding projections 75 of the reel. As shown in FIG. 13, the plane of rotation of the reel may be angled slightly away from the axis of the incoming wire to ensure that the entering wire 21 contacts the side of the reel having projections.

Figure 16:
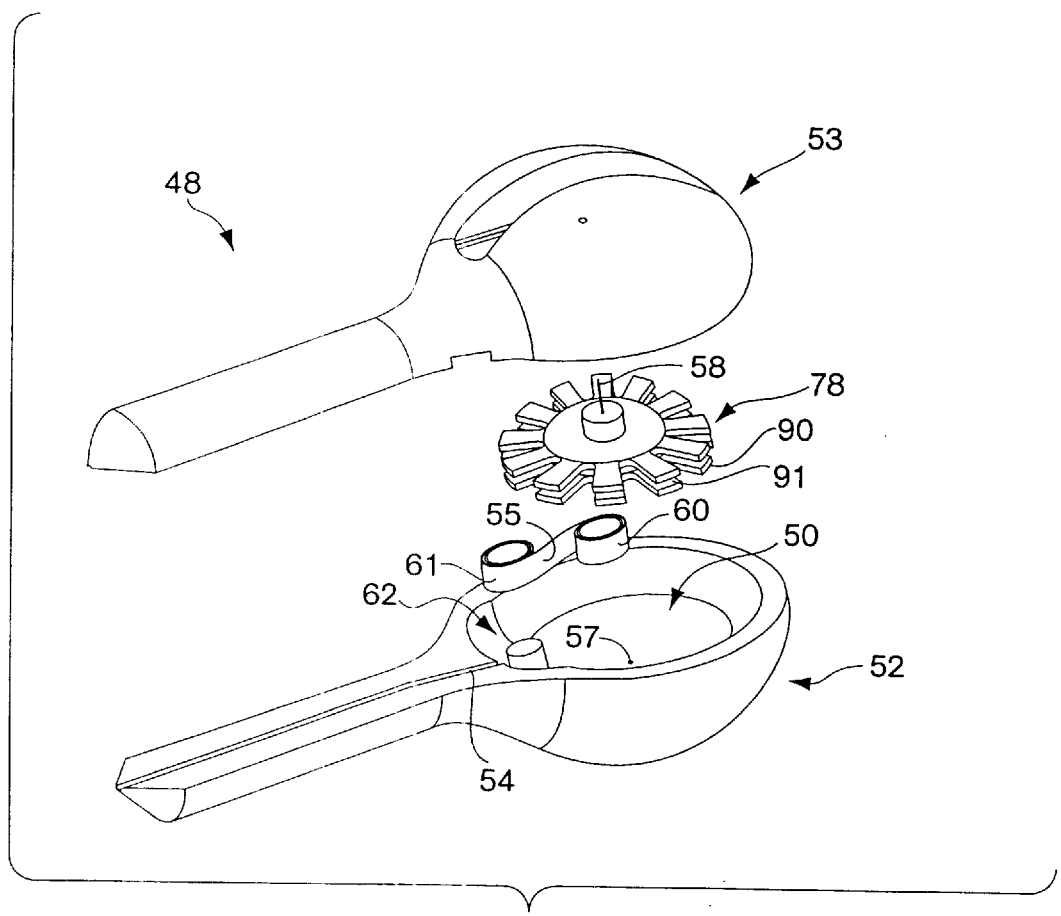
FIG. 16 is an exploded view of a housing having an automatic return spring and a rotatable storage reel that is peripherally defined by a material adapted to engage and capture the wire.
Figure 16A:
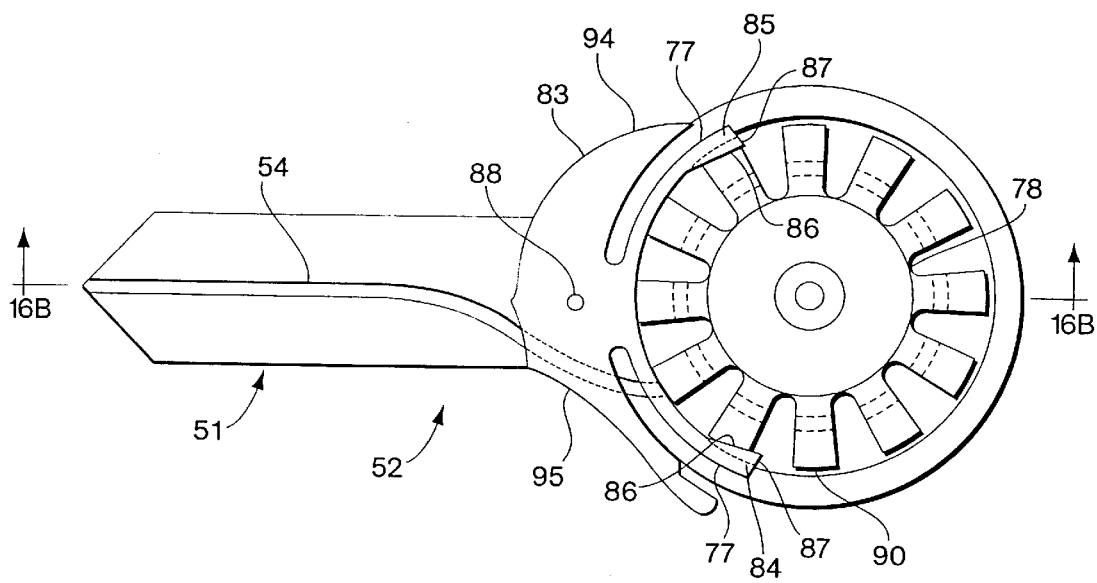
FIG. 16A is a top view of the bottom half of the housing showing the storage reel and the release lever.
Figure 16B:
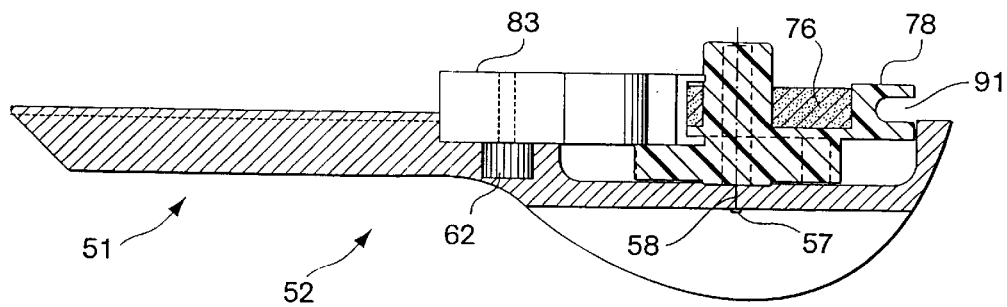
FIG. 16B is a sectional illustration of the bottom half of the housing with the storage reel and the release lever as seen along the line of 16B—16B of FIG. 16A.
Figure 16C:
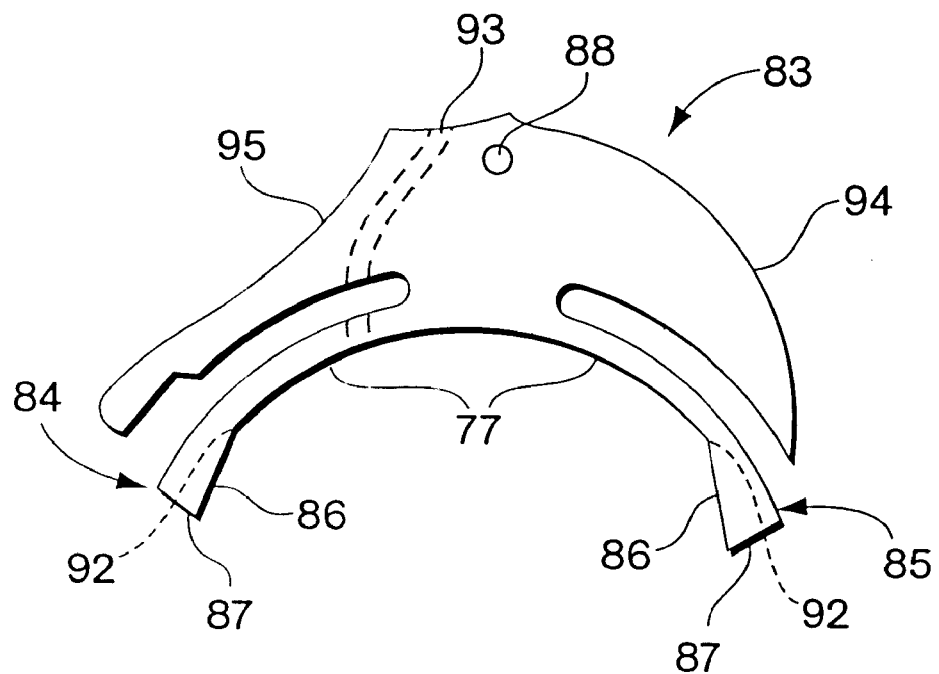
FIG. 16C is a plan illustration of the release lever having pawls at each end.
Figure 16D:
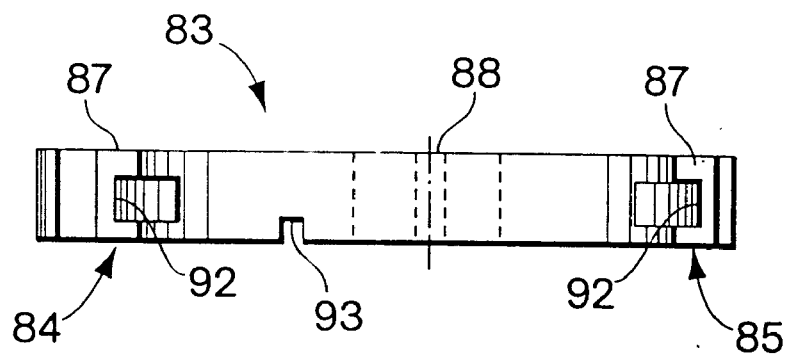
FIG. 16D is a bottom view of the release lever illustrating the channel in each pawl.

FIGS. 16, 16A and 16B show another embodiment of a spring driven device. In this embodiment, instead of a friction brake, the release lever 83 (not shown in FIG. 16) is itself constructed to regulate movement of the wire into or out of the housing. FIG. 16A shows the release lever 83 which is pivotally mounted, at its center 88, between the housing halves 52 and 53 (not shown). The lever 83, as shown in FIG. 16C, has pawls 84 and 85 at each end for engagement with square teeth 90 of the storage reel 78. The pawls are located at the ends of flexible arms 77 extending from the release lever 83. Each of the uncoil pawl 85 and the coil pawl 84 has an angled surface 86, that allows the square teeth 90 of the rotating reel 78 to slip by the pawl, and a flat edge surface 87 that engages the square teeth, stopping rotation of the reel. The bottom side of the release lever of FIG. 16C is shown in FIG. 16D. As shown in FIG. 16D the angled surface of each pawl has channel 92 to provide additional clearance for the coiled wire accumulated around the reel to pass by without pushing the pawl out of contact with the square teeth 90. The release lever 83 also has a groove 93 formed along its surface which corresponds to the path of the bore 54 extending through the neck 51 of the housing. The groove 93 provides a path of travel for the wire through the bore 54 that would otherwise be blocked by the position of the lever on between the housing halves 52 and 53 (not shown). The release lever 83 may be formed from a semi-rigid plastic material which allows some flexibility of the arms 77 to be deflected as the user presses on one side of the lever 83 to raise the pawl on the opposite side out of engagement from the square teeth 90 of the reel 78.

As shown in FIGS. 16E, 16F and 16G, the storage reel may be locked or free to rotate only in the coil or uncoil direction depending on the position of the release lever 83. FIG. 16E shows the release lever positioned to lock the reel 78, preventing rotation and movement of the wire in either direction with respect to the housing. The reel 78 is locked when the lever 83 be pivoted midway, so that both the coil and uncoil pawls, 84 and 85, engage the square teeth 90 of the reel. With both pawls engaged, each flat edge surface 87 will be positioned to contact a square tooth 90, preventing rotation in either direction. Due to the resiliency and flexibility of the arms 77, the force of both pawls against the reel will naturally bias the lever in the locked position when no force is applied by the user.

FIG. 16F shows the release lever 83 pivoted such that the uncoil pawl 85 engages the square teeth 90 of the reel and the coil pawl 84 is raised away from the reel 78. Clockwise (uncoiling) rotation is allowed in this position because the angled surface 86 of the uncoil pawl 85 faces the direction of uncoil rotation and allows approaching square teeth 90 to slip by the pawl. Rotation in the counterclockwise (coil) direction is prevented by the locking interface of the square teeth 90 with the flat edge surface 87 of the uncoil pawl 85.

Therefore, to uncoil wire, the operator need only pivot the release lever 83 to disengage the coil pawl 84 from the square teeth 90 of the reel 78 then manually withdraw wire from the housing.

FIG. 16G shows the release lever pivoted such that the coil pawl 84 engages the square teeth 90, allowing rotation in the coil direction but preventing uncoil rotation. Because the coil pawl 84 is the reverse shape of the uncoil pawl 85, the angled surface 86 of the coil pawl faces the direction of coiling rotation and is deflected out of the way by oncoming square teeth 90. The flat edge surface 87 of the coil pawl 84 catches the square teeth to prevent uncoiling rotation. Pivoting the release lever 83 in this position allows the reel 78 to rotate automatically by the torque provided by the return spring thereby recoiling the wire. The release lever 83 has contours 94 and 95 to orient the user with which side of the release lever should be depressed to coil or uncoil wire. The uncoil contour 94 is convex, shaped outward to signify that depressing this side of the lever releases wire out of the housing. The coil contour 95 is concave, shaped inward to signify that depressing this side of the lever returns the wire into the housing.

Figure 16H:
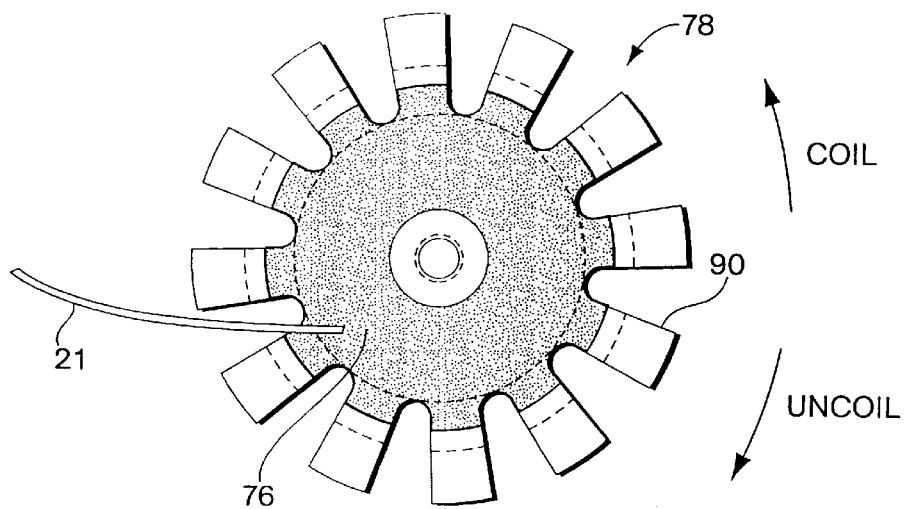
FIG. 16H is a top view of the wire puncturing the pliable gripping material placed around the reel.
Figure 16I:
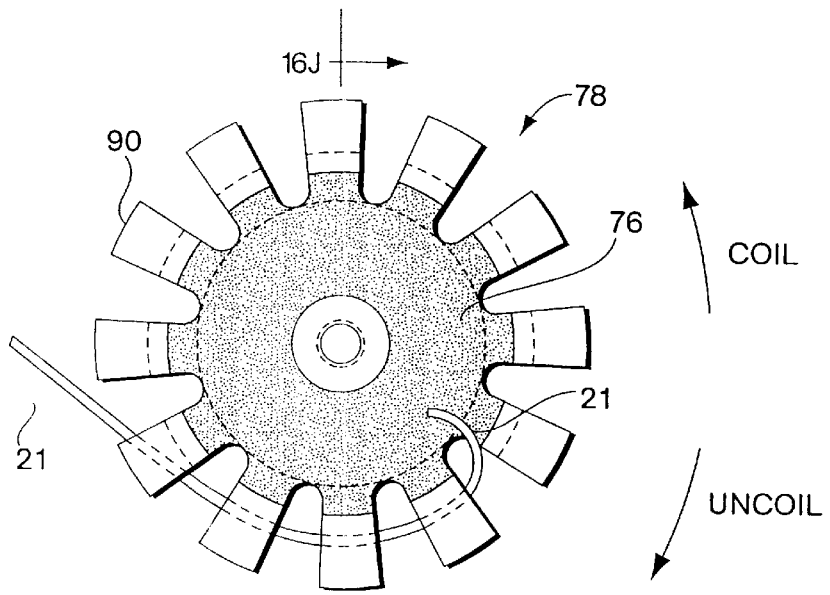
FIG. 16I is a top view of the wire beginning to coil around the storage reel once reel rotation in the coil direction has begun.
Figure 16J:
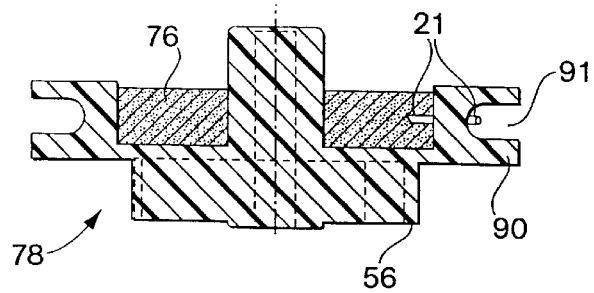
FIG. 16J is a sectional view of the storage reel having pliable gripping material along the line 16J—16J of FIG. 16I.

FIGS. 16H, 16I and 16J show the reel 78 of this housing embodiment having placed around its surface an annulus of pliable gripping material 76 such as silicone sponge type R10470 available from CHR Industries of New Haven, Conn. The material is capable of being pierced by the end of an entering wire 21 as it initially encounters the reel 78. Once the wire 21 pierces the pliable material 76 as shown in FIG. 16H, frictional gripping force is provided as the material resiliently springs back around the puncture site to surround and frictionally engage the wire. The frictional force on the wire is sufficient to resist the pulling force on the wire as the reel 78 begins to rotate as shown in FIG. 16I. The wire is guided to the peripherally disposed gripping material by the orientation of the bore 54 extending through the neck 51 of the housing 48. As it is advanced into the housing, the proximal end of the wire 21, comes into contact with the reel 78 at a location between the square teeth 90 so that it may puncture and become embedded in the gripping material 76. The teeth 90 are spaced around the reel 78 such that when the pawls 84 and 85 of the release lever 83 engage them, the reel will always be positioned to receive the incoming wire 21 between the teeth, so that it may pierce the gripping material 76.

This embodiment of the wire retention system does not require that the reel 78 rotate in a plane that is skewed slightly from the axis of the incoming wire as the gripping foam is located in the center of the reel, in line with the entering wire. Rotating the reel after the end of the wire has been secured in the gripping material, causes the wire to be wound around the perimeter of the reel, positioned in the grooves 91 defined in each square tooth 90 as shown in FIG. 16J. One end of the return spring 55 is wound around the hub 56 of the reel to form the output spool 60 and the other end is wound at the recess holder 62 to form the storage spool 61 of the spring.

Figure 17:
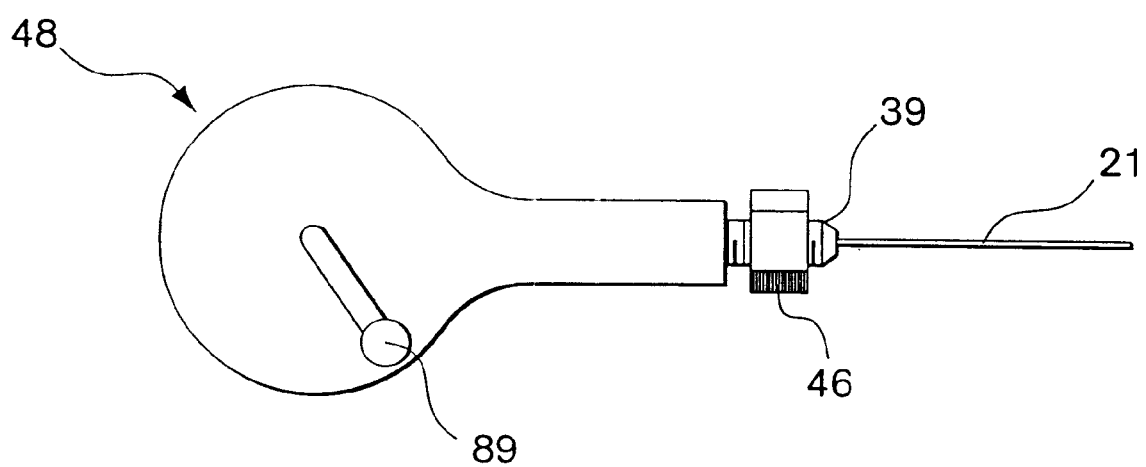
FIG. 17 is an illustration of the housing having a wire storage reel that is manually rotated by means of a crank arm.

Rotatable storage reels such as 49 and 78 described in the above embodiments may be rotated by various other means besides a return spring. As shown in FIG. 17, the reel may be rotated manually by means of a crank arm 89 mounted to the reel at one end with the other, handle end, projecting through the exterior wall of the housing 48. The manually wound reel housing shown in FIG. 17 also may have a wire braking and clamping means such as, for example, the brake described in connection with FIGS. 8 and 9.

Figure 18A:
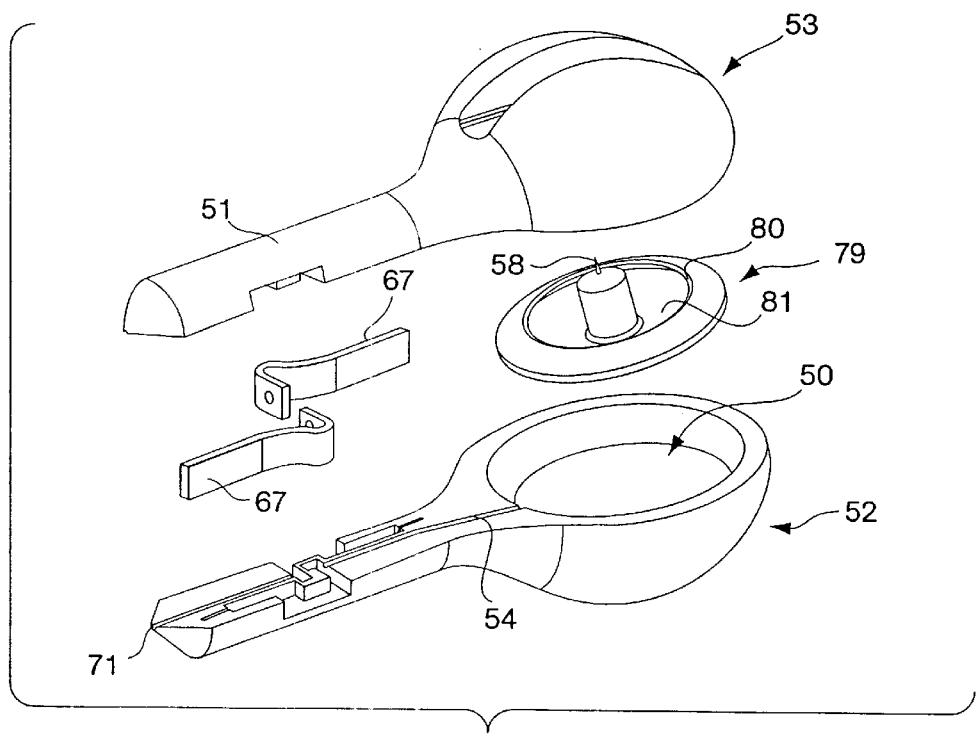
FIG. 18A is an exploded view of a housing having a free-wheeling wire storage reel.
Figure 18B:
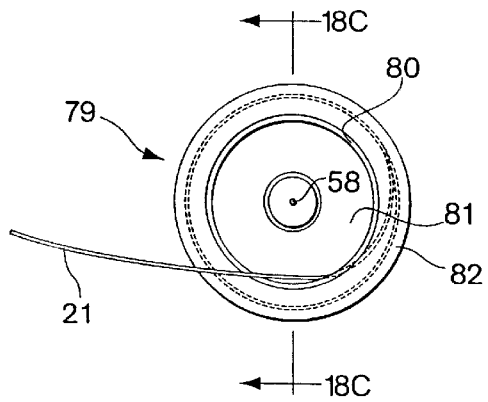
FIG. 18B is a side view of the free-wheeling wire storage reel containing the wire under a projecting lip.
Figure 18C:
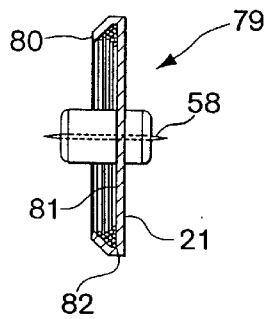
FIG. 18C is a side view of the free-wheeling wire storage reel containing the wire under a projecting lip.

FIGS. 18 and 18A show another embodiment of the rotary reel housing similar to the embodiments shown in FIGS. 13–17 but in which the reel is free-wheeling instead of being spring driven. The housing utilizes a reel 79 depicted in FIGS. 18A, 18B and 18C. The reel 79 has a lip 80 around its circumference that is oriented upwardly inward, toward the center of the reel to define a circumferential corner 82. The wire is retained within the corner 82 defined by the lip 80. The reel 79 is allowed to rotate freely as the wire is being withdrawn from the reel or upon reinsertion of the wire into the reel. As the wire is manually reinserted into the housing, it contacts the facing surface 81 of the reel 79 which directs the wire into the corner 82 and against the lip 80. The reel rotates in a plane that is angled slightly away from the axis of the wire entering the proximal storage portion 50. This orientation of the reel ensures that an incoming wire 21 contacts the facing surface 81 side of the reel 79. Engagement of the wire 21 with the lip 80 creates a moment arm around the axle 58 causing the reel 79 to rotate. As the wire is continually fed into the housing, the reel continues to rotate, collecting the wire under the lip 80. Withdrawal of the wire 21 from the housing likewise causes the reel to rotate to release the wire.

Figure 19:
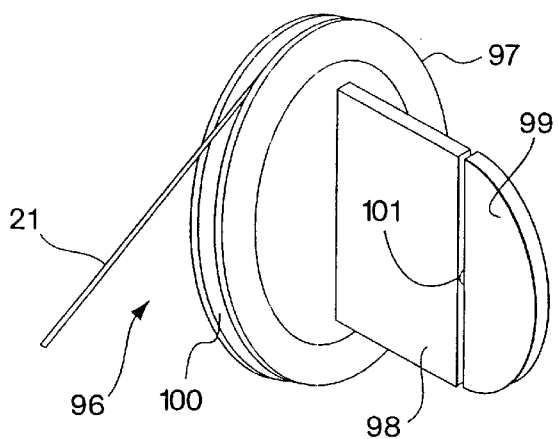
FIG. 19 is an isometric view of an open wire receptacle comprising a spool and a tab for grasping.
Figure 19A:
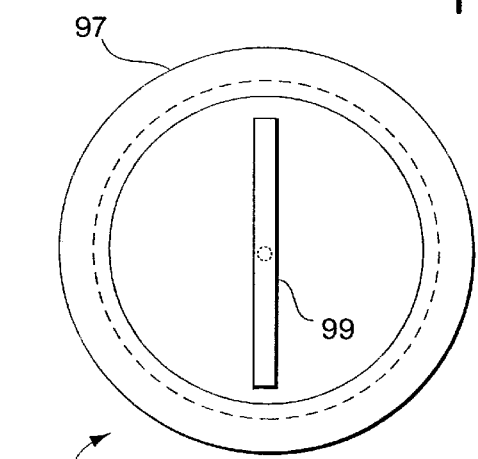
FIG. 19A is a side view of the open wire receptacle comprising a spool and a tab for grasping.
Figure 19B:
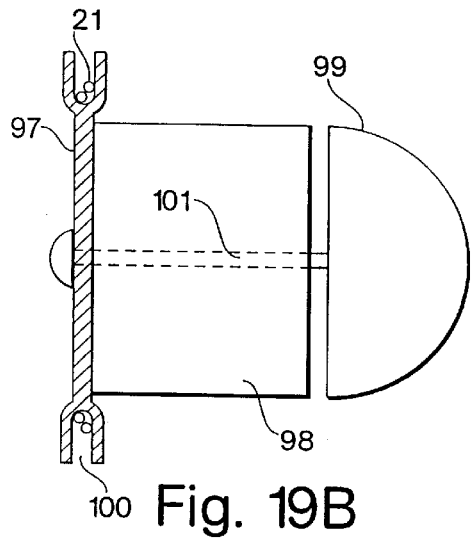
FIG. 19B is a front view of the open wire receptacle comprising a spool and a tab for grasping.

A storage receptacle to hold the proximal extension portion of the wire in its compacted form may take the form of the open wire receptacle shown in FIGS. 19, 19A and 19B. The receptacle may comprise a spool having an inverted U-shaped channel 100 formed around its perimeter to hold the wire 21 and a fixed tab 98 projecting from its side for grasping. The spool and fixed tab are rotatable about a shaft 101 extending through their center. The shaft extends into the center of a tab handle 99 that is gasped by the user to allow the spool 97 and fixed tab 99 to rotate freely to dispense the coiled wire 21. To reload wire around the spool, the fixed tab is grasped to prevent rotation and the wire is manually wound around the spool 97 into the U-shaped channel 100.

Figure 19C:
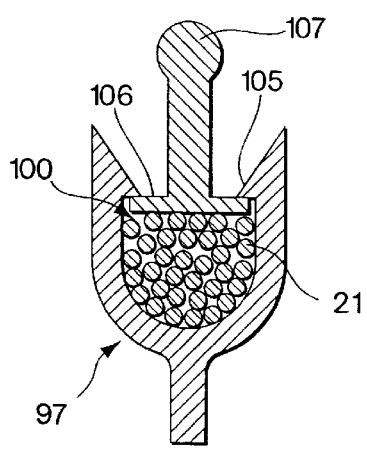
FIG. 19C is a detail of the U-shaped channel of the spool having circumferential shoulders to hold the restraining wrap.
Figure 19D:
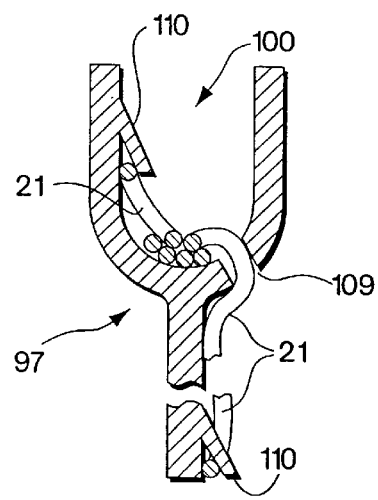
FIG. 19D is a detail of the U-shaped channel of the spool having wire catches formed to pinch and hold the ends of the wire.

FIGS. 19C and 19D shown various means for retaining the coiled wire within the U-shaped channel 100 of the spool. FIG. 19C shows the U-shaped channel having inwardly projecting shoulders 105 extending around the perimeter of the spool 97. The shoulders restrain a pliable restraining wrap 106 within the channel, which covers and retains the wire 21 wrapped around the spool. To release the wire from the reel, the wrap handle 107 is grasped and the wrap 106 pulled past its engagement with the shoulders 105 and away from the spool 97 to free the wire. FIG. 19D shows a wire catch 110 projecting angularly away from the interior wall of the U-shaped channel 100. The end of the wire 21 can be pinched between the converging surfaces of the catch and the wall and restrained from moving. The wire catch 110 can retain the last coil of the wire in the channel after winding is completed, preventing unraveling.

Means of initially catching a wire within the spool to prevent slippage as winding begins may be provided by a catch port 109 formed in the bottom of the U-shaped channel. The catch port 109 is sized to receive the end of the wire, and then pinch and restrain the wire when it is pulled back in the direction of winding. Instead of a catch port, another wire catch 110 can be employed to engage the end of a wire 21 at the lower portion of the spool 97 so that winding can be initiated. While the wire is retained on the spool, the receptacle 96 may be grasped and manipulated to steer the distal portion of the guidewire through the patient's vasculature.

During a catheterization procedure, the storable guidewire system may be used in the following manner. The distal end of the guidewire is inserted into the proximal end of a catheter and advanced until the distal end of the guidewire protrudes from the distal end of the catheter. Once the guidewire has been inserted into the catheter, both are inserted into the artery of the patient. The receptacle containing the proximal extension portion of the guidewire then may be grasped and manipulated, as a conventional steering handle would be used, to steer the distal end of the guidewire through the patient's vasculature to the treatment area.

When the physician desires to remove the catheter without losing guidewire position, such as to exchange the indwelling catheter for a different catheter, the proximal end of the guidewire can be released from its housing. To perform a catheter exchange all of the wire must be withdrawn from the receptacle and the receptacle removed so that the most proximal end of the wire is exposed. The indwelling catheter then can be withdrawn over the proximal portion of the wire. Wire position within the patient is maintained by holding the uncovered part of the wire to resist the frictional force of the withdrawing catheter. After the first catheter has been completely removed from the guidewire, the next catheter can be loaded onto the proximal end of the guidewire and advanced into the patient. Again, the uncovered part of the wire is held to resist any frictional force of the advancing catheter, maintaining wire position so that the new catheter will be directed to the same treatment area in the patient's vasculature.

After the exchange, if the connection joining the proximal and distal portion of the wire is releasable, the proximal portion of the guidewire may be detached from the distal portion of the wire in the same manner as a conventional extension wire. If the connection is permanent, the physician may wish to cut off the proximal portion at the connection point for easier handling. If yet another exchange is anticipated, the physician may decide to leave the wire fully extended for the remainder of the procedure or may return the wire to the receptacle. Several embodiments of the present invention allow the physician to reload the proximal portion of the wire back to the receptacle for storage in a compact configuration until it is needed again.

From the foregoing it will be appreciated that a simpler and more effective method and apparatus for performing catheter exchanges has been presented. The guidewire and receptacle embodiments described above will allow a physician to contain the more flexible proximal extension portion of the guidewire in an easily manageable size until it is needed for an exchange. The receptacle may be grasped and used as a steering handle to guide the more rigid distal portion of the wire through the patient's vasculature to the area of treatment. When the proximal extension portion of the wire is needed for an exchange it may be released from the receptacle to a straight configuration, used, then readily recovered to the receptacle until it is needed for another exchange. After the procedure, the device may be discarded.

It should be understood that the foregoing description of the invention is intended merely to be illustrative thereof and that other embodiments, modifications and equivalents may be apparent to those skilled in the art without departing from its spirit and principles.

Having thus described the invention, what we desire to claim and secure by Letters Patent is:

1. A guidewire and storage system therefor for facilitating an over-the-wire catheter exchange comprising, in combination:
   an elongate flexible guidewire having a proximal end, a distal end, a distal portion and a proximal portion, wherein the guidewire is within a range on the order of 300 to 400 centimeters in length; and
   a compact storage receptacle wherein substantially all of said receptacle is capable of being held completely within the hand of a user, the compact storable receptacle retains the proximal portion of the guidewire in a tightly coiled configuration and is configured to enable the complete removal of the proximal portion therefrom,
   at least the distal portion of the guidewire being formed from a material having sufficient torsional rigidity so that rotation applied to the proximal end of the guidewire is transmitted controllably to the distal end enabling the guidewire to be steerable, and
   at least the proximal portion of the guidewire being formed from a material and being constructed so that upon removal from the receptacle, the proximal portion of the guidewire will return substantially to its elongate, uncoiled configuration.

2. The system as defined in claim 1 wherein the proximal portion of the guidewire is more flexible than the distal portion.

3. A system as defined in claim 2 wherein the proximal portion of the guidewire is constructed to be confined in a coiled configuration of a diameter as small as approximately equal to twenty times the wire diameter, yet returned to a substantially straight configuration when released.

4. The system as defined in claim 2 wherein the proximal portion and distal portions of the guidewire are fabricated from dissimilar materials.

5. The system as defined in claim 2 wherein the distal portion of the guidewire is made from stainless steel and the proximal portion is made from a superelastic material.

6. The system as defined in claim 4 wherein the proximal portion of the guidewire is made from a superelastic titanium-nickel alloy.

7. The system as defined in claim 1 wherein the receptacle further comprises:
   a housing having an access port adapted to enable the proximal portion of the guidewire to be withdrawn from and reloaded into the housing and
   the housing having an interior having surfaces configured to guide the proximal portion of an entering guidewire into its tightly coiled configuration within the housing and to store the compacted guidewire in readiness for withdrawal from the housing.

8. The system as defined in claim 7 wherein the housing further comprises:
   a hollow storage portion shaped to contain the proximal portion of the guidewire in its tightly coiled configuration; and
   a neck disposed between the housing and the access port, the neck having a guidewire-receptive bore oriented to guide the guidewire in a straight configuration as it exits the housing through the bore.

9. The system as defined in claim 7 further comprising a wire storage reel rotatably mounted within the housing for retracting and coiling the guidewire into the housing.

10. A system as defined in claim 9 further comprising:
    means biasing the storage reel in one rotary direction for enabling the reel to wind the guidewire thereon.

11. The system as defined in claim 10 wherein the biasing means comprises an automatic return spring connected to the wire storage reel capable of providing rotational force to the guidewire storage reel.

12. The system as defined in claim 11 further comprising:
    a release lever pivotally mounted to the housing, accessible from outside the housing and having at least one pawl extending within the housing therefrom and the reel having teeth formed around its circumference that are engagable with the pawl of the release lever.

13. The system as defined in claim 10 wherein the housing further comprises:

a guidewire braking assembly mounted on the housing, the braking assembly having a portion of which engages the guidewire to regulate the rate at which the guidewire is drawn into the housing.

14. An extension wire for connection to a guidewire and storage system therefor for facilitating an over-the-wire catheter exchange comprising:

an elongated flexible shaft sufficiently flexible to be formed into a coiled configuration; and a compact storage receptacle capable of being held completely within the hand of a user, and shaped and sized to contain the shaft in a tightly coiled configuration, the receptacle being configured to enable the complete removal of the shaft therefrom, the shaft being formed from a material and being constructed so that upon removal from the receptacle the shaft will substantially return to its elongate, uncoiled configuration, and the combination of the extension wire connected to the guidewire being within a range on the order of 300 to 400 centimeters in length.

15. A guidewire and storage system therefor for facilitating an over-the-wire catheter exchange comprising:

an elongate flexible guidewire having a proximal end, a distal end, a distal portion and a proximal portion, wherein the guidewire is within a range on the order of 300 to 400 centimeters in length; and a compact storage housing having a hollow storage portion capable of being held completely within the hand of a user, the housing having a wire storage reel rotatably mounted within, upon which the proximal portion of the guidewire is tightly wound for storage, and a neck having a bore longitudinally extending from the hollow storage portion to the outside of the housing through which the wire passes to and from the storage portion, the housing being configured to enable the complete removal of the proximal portion therefrom, at least the distal portion of the guidewire being formed from a material having sufficient torsional rigidity so that rotation applied to the proximal end of the guidewire is transmitted controllably to the distal end enabling the guidewire to be steerable, and at least the proximal portion of the guidewire being formed from a material and being constructed so that upon removal from the housing, the proximal portion of the guidewire will substantially return to its elongate, uncoiled configuration.

16. A guidewire and storage system therefor for facilitating an over-the-wire catheter exchange comprising:

an elongate flexible guidewire having a proximal end, a distal end, a distal portion and a proximal portion, wherein the guidewire is within a range on the order of 300 to 400 centimeters in length; and a compact storage housing capable of being held completely within the hand of a user having internal dimensions adapted to contain the proximal portion of the guidewire in a tightly coiled configuration, the housing being configured to enable the complete removal of the proximal portion of the guidewire therefrom and having means for slowing and stopping movement of the guidewire into or out of the housing, at least the distal portion of the guidewire being formed from a material having sufficient torsional rigidity so that rotation applied to the proximal end of the guidewire is transmitted controllably to the distal end thereby enabling the guidewire to be steerable, and at least the proximal portion of the guidewire being formed from a material and being constructed so that upon removal from the housing, the proximal portion of the guidewire will substantially return to its elongate, uncoiled configuration.

17. A guidewire and storage system therefor for facilitating an over-the-wire catheter exchange comprising:

an elongate flexible guidewire having a proximal end, a distal end, a distal portion and a proximal portion, wherein the guidewire is within a range on the order of 300 to 400 centimeters in length; and an open compact storage receptacle capable of being held completely within the hand of a user, adapted to retain the proximal portion of the guidewire in a tightly coiled configuration, and configured to enable the complete removal of the proximal portion of the guidewire therefrom and return thereto, at least the distal portion of the guidewire being formed from a material having sufficient torsional rigidity so that rotation applied to the proximal end of the guidewire is transmitted controllably to the distal end thereby enabling the guidewire to be steerable, and at least the proximal portion of the guidewire being formed from a material and being constructed so that upon removal from the receptacle, the proximal portion of the guidewire will substantially return to its elongate, uncoiled configuration.

18. A guidewire and storage system therefor comprising:

an elongate flexible guidewire having a proximal end, a distal end and a proximal portion; and a compact storage receptacle, wherein the compact storage receptacle retains the proximal portion of the guidewire in a tightly coiled configuration and is configured to enable the removal of the proximal portion therefrom, said receptacle comprising a housing having an access port adapted to enable the proximal portion of the guidewire to be withdrawn from and reloaded into the housing and said housing containing internal members constructed and arranged to cause the proximal portion of the wire to be reformed to its tightly coiled configuration within the housing and to store the compacted wire in readiness for withdrawal from the housing, wherein at least the proximal portion of said guidewire is configured so that upon removal from the housing, the proximal portion of the guidewire will return substantially to its elongate, uncoiled configuration, wherein said internal members comprise the interior of the housing having surfaces contoured to direct the proximal portion of the guidewire into a coiled configuration and to retain the wire in the coiled configuration and a wire storage reel rotatably mounted within the housing, and wherein an automatic return spring is connected to and provides rotational force to the wire storage reel to bias said storage reel in one rotary direction for enabling said storage reel to wind the wire thereon.

19. The system as defined in claim 18 further comprising:

a release lever at least partially disposed in said housing having at least one pawl and being pivotally mounted to the housing;

wherein the reel has teeth formed around its circumference that are engagable with the pawl of the release lever.

20. A guidewire and storage system therefor comprising an elongate flexible guidewire having a proximal end, a distal end and a proximal portion; and a compact storage receptacle retaining the proximal portion of the guidewire in a tightly coiled configuration, the receptacle being configured to enable the removal of the proximal portion therefrom, said receptacle comprising a housing having an access port adapted to enable the proximal portion of the guidewire to be withdrawn from and reloaded into the housing and said housing containing internal members constructed and arranged to cause the proximal portion of the wire to be reformed to its tightly coiled configuration within the housing and to store the coiled wire in readiness for withdrawal from the housing, wherein at least the proximal portion of said guidewire is configured so that upon removal from the housing, the proximal portion of the guidewire will return substantially to its elongate, uncoiled configuration, and wherein said internal members comprise the interior of the housing having surfaces contoured to direct the proximal portion of the guidewire into a coiled configuration and to retain the wire in the coiled configuration and a wire storage reel rotatably mounted within the housing;

means biasing the storage reel in one rotary direction for enabling the reel to wind the wire thereon; and a wire braking assembly mounted on and at least partially within the housing.

* * * * *